(12) United States Patent
Iguchi

(10) Patent No.: US 8,748,590 B2
(45) Date of Patent: Jun. 10, 2014

(54) OLIGONUCLEOTIDES FOR DETECTION TEST OF POLYMORPHISM OF EGFR EXON 19 AND USE THEROF

(75) Inventor: Aki Iguchi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 13/461,406

(22) Filed: May 1, 2012

(65) Prior Publication Data

US 2012/0282610 A1    Nov. 8, 2012

(30) Foreign Application Priority Data

May 6, 2011    (JP) .................................. 2011-103818
Apr. 17, 2012  (JP) .................................. 2012-094081

(51) Int. Cl.
| | | |
|---|---|---|
| C07H 21/02 | (2006.01) | |
| C07H 21/04 | (2006.01) | |
| C12Q 1/68  | (2006.01) | |
| C12P 19/34 | (2006.01) | |

(52) U.S. Cl.
USPC ........ 536/23.1; 536/24.33; 435/6.1; 435/91.2

(58) Field of Classification Search
None
See application file for complete search history.

(56) References Cited

U.S. PATENT DOCUMENTS

| 7,932,026 B2 * | 4/2011 | Seshagiri ..................... 435/6.11 |
| 2007/0235658 A1 | 10/2007 | Zimdars et al. |
| 2010/0216123 A1 * | 8/2010 | Hirai et al. ........................ 435/6 |
| 2011/0186738 A1 | 8/2011 | Itozaki |

FOREIGN PATENT DOCUMENTS

| JP | 2002-119291 A | 4/2002 |
| WO | 2010/001969 A1 | 1/2010 |

OTHER PUBLICATIONS

Mitsudomi et al., "Mutations of the Epidermal Growth Factor Receptor Gene Predict Prolonged Survival After Gefitinib Treatment in Patients With Non-Small-Cell Lung Cancer With Postoperative Recurrence," Journal of Clinical Oncology, 23:2513-2520 (2005).
Pao et al., "Acquired Resisance of Lung Adenocarcnomas to Gefitnib or Erlotinib is Associaed wth a Second Mutation in the EGFR Kinase Domain," PLoS Medicine, 2: 225-235 (2005).

* cited by examiner

Primary Examiner — Stephen Kapushoc
(74) Attorney, Agent, or Firm — Morgan, Lewis & Bockius LLP

(57) ABSTRACT

An oligonucleotide for a detection test of a polymorphism of EGFR exon 19, the oligonucleotide being at least one selected from the group consisting of a P1 oligonucleotide and a P1' oligonucleotide, the P1 oligonucleotide having a 3' end subjected to an extension inhibition treatment, which has an identity of at least 80% with respect to a base sequence including at least the 115th to the 123rd bases of the base sequence indicated in SEQ ID NO: 1 and has a length of from 9 to 80 bases; and the P1' oligonucleotide having a 3' end subjected to an extension inhibition treatment, which hybridizes under stringent conditions with a complementary strand of a base sequence including at least the 115th to the 123rd bases of the base sequence indicated in SEQ ID NO: 1 and having a length of from 9 to 80 bases.

13 Claims, 9 Drawing Sheets

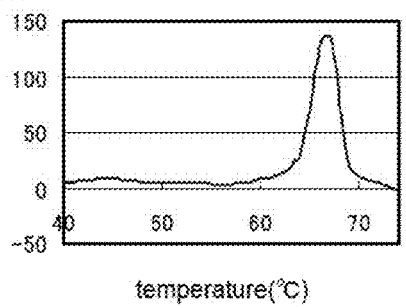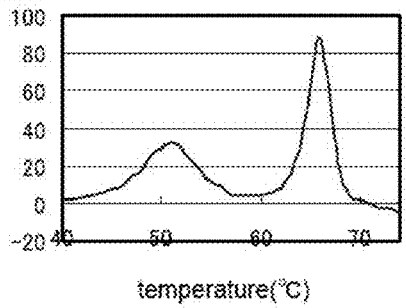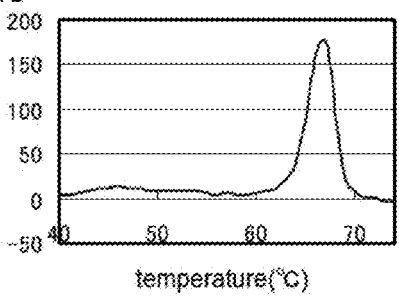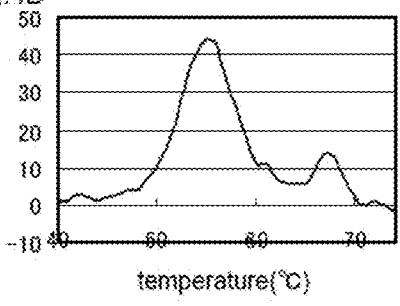

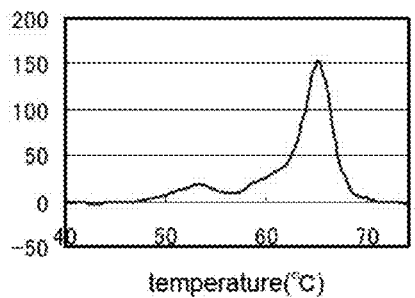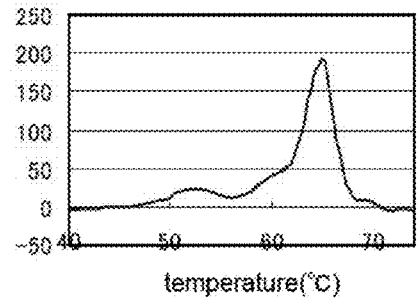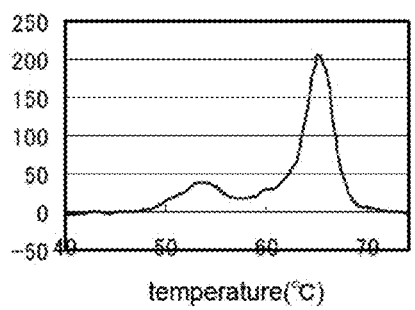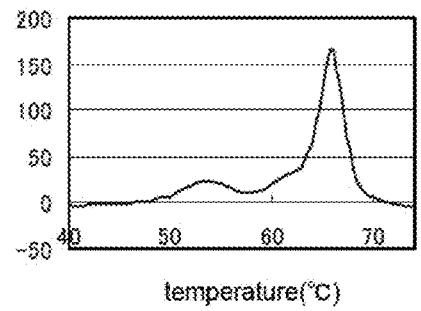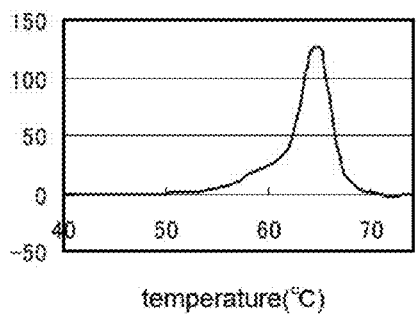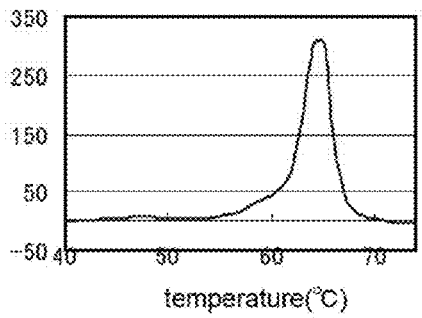

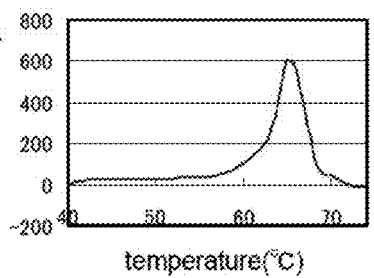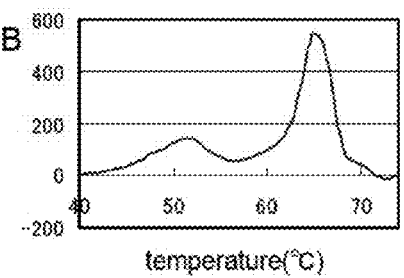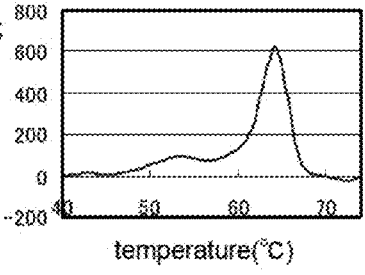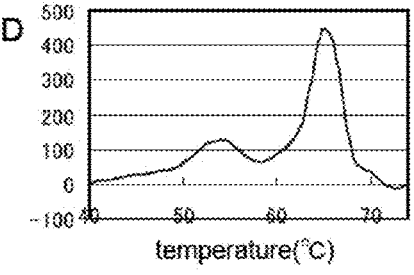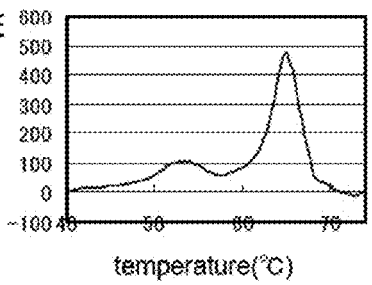

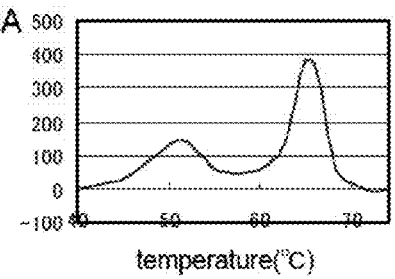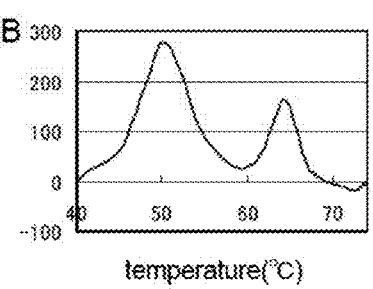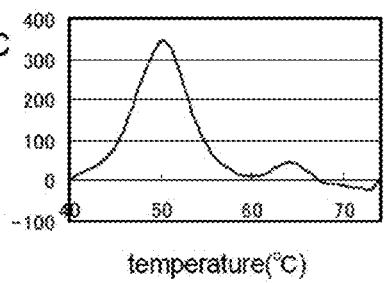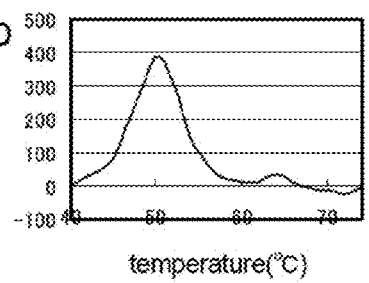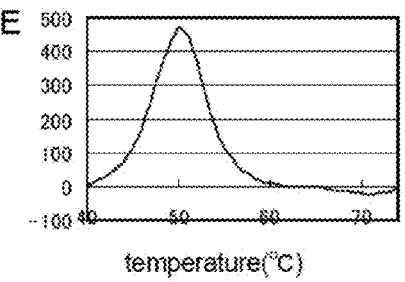

SEQUENCE LISTING

<160> NUMBER OF SEQ ID NOS: 39

<210> SEQ ID NO 1
<211> LENGTH: 287
<212> TYPE: DNA
<213> ORGANISM: Homo sapiens

<400> SEQUENCE: 1

```
tcactgggca gcatgtggca ccatctcaca attgccagtt aacgtcttcc ttctctctct      60
gtcataggga ctctggatcc cagaaggtga gaaagttaaa attcccgtcg ctatcaagga     120
attaagagaa gcaacatctc cgaaagccaa caaggaaatc ctcgatgtga gtttctgctt     180
tgctgtgtgg gggtccatgg ctctgaacct caggcccacc tttctcatg tctggcagct      240 gctctgctct agaccctgct catctccaca tcctaaatgt tcacttt                   287
```

<210> SEQ ID NO 2
<211> LENGTH: 40
<212> TYPE: DNA
<213> ORGANISM: Artificial
<220> FEATURE:
<223> OTHER INFORMATION: Cmp-1

<400> SEQUENCE: 2

```
cccgtcgcta tcaaggaatt aagagaagca acatctccga                            40
```

<210> SEQ ID NO 3
<211> LENGTH: 29
<212> TYPE: DNA
<213> ORGANISM: Artificial
<220> FEATURE:
<223> OTHER INFORMATION: Cmp-2

<400> SEQUENCE: 3

```
cccgtcgcta tcaaggaatt aagagaagc                                    29
```

<210> SEQ ID NO 4
<211> LENGTH: 28
<212> TYPE: DNA
<213> ORGANISM: Artificial
<220> FEATURE:
<223> OTHER INFORMATION: Cmp-3

<400> SEQUENCE: 4

```
caaggaatta agagaagcaa catctccg                                     28
```

<210> SEQ ID NO 5
<211> LENGTH: 49
<212> TYPE: DNA
<213> ORGANISM: Artificial
<220> FEATURE:
<223> OTHER INFORMATION: Cmp-4

<400> SEQUENCE: 5

```
gagaaagtta aaattcccgt cgctatcaag gaattaagag aagcaacat              49
```

<210> SEQ ID NO 6
<211> LENGTH: 47
<212> TYPE: DNA
<213> ORGANISM: Artificial
<220> FEATURE:
<223> OTHER INFORMATION: Cmp-5

<400> SEQUENCE: 6

```
cccagaaggt gagaaagtta aaattcccgt cgctatcaag gaattaa                47
```

<210> SEQ ID NO 7
<211> LENGTH: 36
<212> TYPE: DNA
<213> ORGANISM: Artificial
<220> FEATURE:
<223> OTHER INFORMATION: Cmp-6

<400> SEQUENCE: 7

```
gtcgctatca aggaattaag agaagcaaca tctccg                            36
```

<210> SEQ ID NO 8
<211> LENGTH: 20
<212> TYPE: DNA
<213> ORGANISM: Artificial
<220> FEATURE:
<223> OTHER INFORMATION: Cmp-7

<400> SEQUENCE: 8

```
cccgtcgcta tcaaggaatt                                              20
```

<210> SEQ ID NO 9
<211> LENGTH: 80
<212> TYPE: DNA
<213> ORGANISM: Artificial
<220> FEATURE:
<223> OTHER INFORMATION: Cmp-8

<400> SEQUENCE: 9

```
cccgtcgcta tcaaggaatt aagagaagca acatctccga aagccaacaa ggaaatcctc  60
gatgtgagtt tctgctttgc                                              80
```

<210> SEQ ID NO 10
<211> LENGTH: 80

```
<212> TYPE: DNA
<213> ORGANISM: Artificial
<220> FEATURE:
<223> OTHER INFORMATION: Cmp-9

<400> SEQUENCE: 10
catagggact ctggatccca gaaggtgaga agttaaaat tcccgtcgct atcaaggaat    60
taagagaagc aacatctccg                                              80

<210> SEQ ID NO 11
<211> LENGTH: 39
<212> TYPE: DNA
<213> ORGANISM: Artificial
<220> FEATURE:
<223> OTHER INFORMATION: Cmp-10

<400> SEQUENCE: 11
ccgtcgctat caaggaatta agagaagcaa catctccga                         39

<210> SEQ ID NO 12
<211> LENGTH: 38
<212> TYPE: DNA
<213> ORGANISM: Artificial
<220> FEATURE:
<223> OTHER INFORMATION: Cmp-11

<400> SEQUENCE: 12
cgtcgctatc aaggaattaa gagaagcaac atctccga                          38

<210> SEQ ID NO 13
<211> LENGTH: 33
<212> TYPE: DNA
<213> ORGANISM: Artificial
<220> FEATURE:
<223> OTHER INFORMATION: Cmp-12

<400> SEQUENCE: 13
ctatcaagga attaagagaa gcaacatctc cga                               33

<210> SEQ ID NO 14
<211> LENGTH: 29
<212> TYPE: DNA
<213> ORGANISM: Artificial
<220> FEATURE:
<223> OTHER INFORMATION: Cmp-13

<400> SEQUENCE: 14
caaggaatta agagaagcaa catctccga                                    29

<210> SEQ ID NO 15
<211> LENGTH: 10
<212> TYPE: DNA
<213> ORGANISM: Artificial
<220> FEATURE:
<223> OTHER INFORMATION: Cmp-14

<400> SEQUENCE: 15
caaggaatta                                                         10

<210> SEQ ID NO 16
<211> LENGTH: 78
<212> TYPE: DNA
<213> ORGANISM: Artificial
<220> FEATURE:
<223> OTHER INFORMATION: Cmp-15

<400> SEQUENCE: 16
```

-continued

```
cgtcgctatc aaggaattaa gagaagcaac atctccgaaa gccaacaagg aaatcctcga      60
tgtgagtttc tgctttgc                                                    78

<210> SEQ ID NO 17
<211> LENGTH: 48
<212> TYPE: DNA
<213> ORGANISM: Homo sapiens

<400> SEQUENCE: 17
cccgtcgcta tcaaggaatt aagagaagca acatctccga aagccaac                   48

<210> SEQ ID NO 18
<211> LENGTH: 33
<212> TYPE: DNA
<213> ORGANISM: Homo sapiens

<400> SEQUENCE: 18
gccgtcgcta tcaaaacatc tccgaaagcc aac                                   33

<210> SEQ ID NO 19
<211> LENGTH: 33
<212> TYPE: DNA
<213> ORGANISM: Homo sapiens

<400> SEQUENCE: 19
gccgtcgcta tcaagacatc tccgaaagcc aac                                   33

<210> SEQ ID NO 20
<211> LENGTH: 38
<212> TYPE: DNA
<213> ORGANISM: Homo sapiens

<400> SEQUENCE: 20
gccgtcgcta tcaaggaaca acatctccga aagccaac                              38

<210> SEQ ID NO 21
<211> LENGTH: 33
<212> TYPE: DNA
<213> ORGANISM: Homo sapiens

<400> SEQUENCE: 21
gccgtcgcta tcaaggaatc tccgaaagcc aac                                   33

<210> SEQ ID NO 22
<211> LENGTH: 30
<212> TYPE: DNA
<213> ORGANISM: Homo sapiens

<400> SEQUENCE: 22
gccgtcgcta tcaaggaatc gaaagccaac                                       30

<210> SEQ ID NO 23
<211> LENGTH: 36
<212> TYPE: DNA
<213> ORGANISM: Homo sapiens

<400> SEQUENCE: 23
gccgtcgcta tcaaggaacc atctccgaaa gccaac                                36

<210> SEQ ID NO 24
<211> LENGTH: 30
<212> TYPE: DNA
<213> ORGANISM: Homo sapiens
```

```
<400> SEQUENCE: 24
gccgtcgcta tcaaggaacc gaaagccaac                                30

<210> SEQ ID NO 25
<211> LENGTH: 30
<212> TYPE: DNA
<213> ORGANISM: Homo sapiens

<400> SEQUENCE: 25
gccgtcgcta tcaaggttcc gaaagccaac                                30

<210> SEQ ID NO 26
<211> LENGTH: 36
<212> TYPE: DNA
<213> ORGANISM: Homo sapiens

<400> SEQUENCE: 26
gccgtcgcta tcaaggaatc atctccgaaa gccaac                         36

<210> SEQ ID NO 27
<211> LENGTH: 30
<212> TYPE: DNA
<213> ORGANISM: Homo sapiens

<400> SEQUENCE: 27
gccgtcgcta tcaaggaaca gaaagccaac                                30

<210> SEQ ID NO 28
<211> LENGTH: 33
<212> TYPE: DNA
<213> ORGANISM: Homo sapiens

<400> SEQUENCE: 28
gccgtcgcta tcaaggtatc tccgaaagcc aac                            33

<210> SEQ ID NO 29
<211> LENGTH: 30
<212> TYPE: DNA
<213> ORGANISM: Homo sapiens

<400> SEQUENCE: 29
gccgtcgcta tcaaggttcc gaaagccaac                                30

<210> SEQ ID NO 30
<211> LENGTH: 30
<212> TYPE: DNA
<213> ORGANISM: Homo sapiens

<400> SEQUENCE: 30
gccgtcgcta tcaaaattcc gaaagccaac                                30

<210> SEQ ID NO 31
<211> LENGTH: 33
<212> TYPE: DNA
<213> ORGANISM: Homo sapiens

<400> SEQUENCE: 31
gccgtcgcta tcaaggaaca accgaaagcc aac                            33

<210> SEQ ID NO 32
<211> LENGTH: 29
<212> TYPE: DNA
<213> ORGANISM: Artificial
```

```
<220> FEATURE:
<223> OTHER INFORMATION: Cmp-C1

<400> SEQUENCE: 32
taagagaagc aacatctccg aaagccaac                                        29

<210> SEQ ID NO 33
<211> LENGTH: 19
<212> TYPE: DNA
<213> ORGANISM: Artificial
<220> FEATURE:
<223> OTHER INFORMATION: EGFR-EX19-F2

<400> SEQUENCE: 33
ctctctgtca tagggactc                                                   19

<210> SEQ ID NO 34
<211> LENGTH: 21
<212> TYPE: DNA
<213> ORGANISM: Artificial
<220> FEATURE:
<223> OTHER INFORMATION: EGFR-EX19-R1

<400> SEQUENCE: 34
gaaactcaca tcgaggattt c                                                21

<210> SEQ ID NO 35
<211> LENGTH: 33
<212> TYPE: DNA
<213> ORGANISM: Artificial
<220> FEATURE:
<223> OTHER INFORMATION: 5FP-EGFR-EX19-WT-FW-3

<400> SEQUENCE: 35
cccgtcgcta tcaagtaatt aagagaagca aca                                   33

<210> SEQ ID NO 36
<211> LENGTH: 287
<212> TYPE: DNA
<213> ORGANISM: Artificial
<220> FEATURE:
<223> OTHER INFORMATION: EGFR exon19 del mutant No.2

<400> SEQUENCE: 36
taacatccac ccagatcact gggcagcatg tggcaccatc tcacaattgc cagttaacgt      60
cttccttctc tctctgtcat agggactctg gatcccagaa ggtgagaaag ttaaaattcc     120
cgtcgctatc aaaacatctc cgaaagccaa caaggaaatc ctcgatgtga gtttctgctt    180
tgctgtgtgg gggtccatgg ctctgaacct caggcccacc ttttctcatg tctggcagct    240
gctctgctct agaccctgct catctccaca tcctaaatgt tcacttt                  287

<210> SEQ ID NO 37
<211> LENGTH: 287
<212> TYPE: DNA
<213> ORGANISM: Artificial
<220> FEATURE:
<223> OTHER INFORMATION: EGFR exon19 del mutant No.3

<400> SEQUENCE: 37
taacatccac ccagatcact gggcagcatg tggcaccatc tcacaattgc cagttaacgt      60
cttccttctc tctctgtcat agggactctg gatcccagaa ggtgagaaag ttaaaattcc     120
cgtcgctatc aagacatctc cgaaagccaa caaggaaatc ctcgatgtga gtttctgctt    180
tgctgtgtgg gggtccatgg ctctgaacct caggcccacc ttttctcatg tctggcagct    240
```

```
gctctgctct agaccctgct catctccaca tcctaaatgt tcacttt        287

<210> SEQ ID NO 38
<211> LENGTH: 288
<212> TYPE: DNA
<213> ORGANISM: Artificial
<220> FEATURE:
<223> OTHER INFORMATION: EGFR exon19 del  mutant No.4

<400> SEQUENCE: 38
ccacccagat cactgggcag catgtggcac catctcacaa ttgccagtta acgtcttcct    60
tctctctctg tcatagggac tctggatccc agaaggtgag aaagttaaaa ttcccgtcgc   120
tatcaaggaa ccaacatctc cgaaagccaa caaggaaatc ctcgatgtga gtttctgctt   180
tgctgtgtgg gggtccatgg ctctgaacct caggcccacc tttctcatg tctggcagct    240 gctctgctct agaccctgct catctccaca tcctaaatgt tcactttc               288

<210> SEQ ID NO 39
<211> LENGTH: 288
<212> TYPE: DNA
<213> ORGANISM: Artificial
<220> FEATURE:
<223> OTHER INFORMATION: EGFR exon19 del  mutant No.6

<400> SEQUENCE: 39
tggtaacatc cacccagatc actgggcagc atgtggcacc atctcacaat tgccagttaa    60
cgtcttcctt ctctctctgt catagggact ctggatccca gaaggtgaga aagttaaaat   120
tcccgtcgct atcaaggaat cgaaagccaa caaggaaatc ctcgatgtga gtttctgctt   180
tgctgtgtgg gggtccatgg ctctgaacct caggcccacc tttctcatg tctggcagct    240 gctctgctct agaccctgct catctccaca tcctaaatgt tcactttc               288
```

OLIGONUCLEOTIDES FOR DETECTION TEST OF POLYMORPHISM OF EGFR EXON 19 AND USE THEROF

CROSS-REFERENCE TO RELATED APPLICATION

This application claims priority under 35 USC 119 from Japanese Patent Application No. 2011-103818 filed on May 6, 2011, and Japanese Patent Application No. 2012-094081 filed on Apr. 17, 2012, the disclosures of which are incorporated by reference herein.

SEQUENCE LISTING SUBMISSION VIA EFS-WEB

A computer readable text file, entitled "SequenceListing.txt," created on or about Jul. 30, 2013 with a file size of about 9 kb contains the sequence listing for this application and is hereby incorporated by reference in its entirety.

BACKGROUND

1. Technical Field

The present invention relates to an oligonucleotide for a detection test of polymorphism of EGFR exon 19 and use thereof.

2. Related Art

An epidermal growth factor receptor (EGFR) is considered to play important roles in lung cancer, and drugs intended to suppress the function of EGFR are used in the field of the treatment of lung cancer. As such drugs, EGFR tyrosine kinase inhibitors such as gefitinib, erlotinib and the like used in the treatment of patients with non-small-cell lung cancer are known, and as for such drugs, an application to adenocarcinoma in addition to the lung cancer is being attempted. However, the effect of the EGFR tyrosine kinase inhibitors may not be obtained sufficiently for a certain range of patients. Another range of patients respond to the EGFR tyrosine kinase inhibitors in the early stages, but the drugs may not become effective beyond expectation gradually.

Therefore, a search of predictive factors to predict the effects of the EGFR tyrosine kinase inhibitors was attempted in order to use the inhibitors, and a mutation of EGFR gene has been found to be an important factor (see, for example, *PLoS Medicine*, 2005, Vol. 2, No. 3, pp. 225-235; and *Journal of Clinical Oncology*, 2005, Vol. 23, No. 11, pp. 2513-2520).

As for mutations related to drug sensitivity, for example, a substitution mutation at 790th and 858th in EGFR gene, a deletion mutation at exon 19 in EGFR gene, and the like are known (see, for example, *PLoS Medicine*, 2005, Vol. 2, No. 3, pp. 225-235; and *Journal of Clinical Oncology*, 2005, Vol. 23, No. 11, pp. 2513-2520). In particular, as for the deletion mutation at exon 19 in EGFR gene, plural mutant types in which consecutive several bases to ten and several bases are deleted in the above-described exon 19 are known.

On the other hand, in recent years, detections utilizing melting curve analysis (Tm analysis) have been carried out as detection tests for detecting genetic polymorphism. In this method, after amplifying a region including a mutation by PCR method, the melting curve analysis is carried out by using a nucleic acid probe labeled with a fluorescent dye, and the mutation of the base sequence is analyzed based on the results of the melting curve analysis (see, for example, Japanese Patent Application Laid-Open (JA-A) No. 2002-119291).

As for a method of detecting a polymorphism easily and with high sensitivity and high reliability, a method of detecting a polymorphism including using a mutant type primer and a wild type (normal type) primer in the same reaction system to amplify a nucleic acid sequence having a mutant type base preferentially is known (see, for example, WO 2010/001969).

SUMMARY OF THE INVENTION

However, as for the mutation of the EGFR exon 19, various mutations exist as described above, so that in a detection test using a primer corresponding to each mutation, a number of primers specific to the mutant types must be contained in a reaction solution. The design of a primer may be complicated by preparing a number of primers, and the PCR reaction itself may come to a stop due to using plural primers at the same time. When plural mutations exist, the polymorphism may not be detected unless the mutations are contained at a sufficient rate.

Accordingly, an object of the present invention is to provide an oligonucleotide for a detection test of a polymorphism and usage thereof, which oligonucleotide is useful for detecting a polymorphism of the EGFR exon 19 easily with high sensitivity in a detection test of the polymorphism thereof.

Aspects of the present invention provide the following oligonucleotide for a detection test of a polymorphism of EGFR exon 19, a method of detecting a polymorphism, a method of evaluating drug efficacy or tolerance and a reagent kit for a detection test of a polymorphism of EGFR exon 19:

[1] An oligonucleotide for a detection test of a polymorphism of EGFR exon 19, the oligonucleotide being at least one selected from the group consisting of a P1 oligonucleotide and a P1' oligonucleotide, the P1 oligonucleotide having a 3' end subjected to an extension inhibition treatment, which has an identity of at least 80% with respect to a base sequence including at least the 115th to the 123rd bases of the base sequence indicated in SEQ ID NO: 1 and has a length of from 9 to 80 bases; and the P1' oligonucleotide having a 3' end subjected to an extension inhibition treatment, which hybridizes under stringent conditions with a complementary strand of a base sequence including at least the 115th to the 123rd bases of the base sequence indicated in SEQ ID NO: 1 and having a length of from 9 to 80 bases.

[2] The oligonucleotide for a detection test of a polymorphism according to claim 1, wherein the oligonucleotide is at least one selected from the group consisting of a P2 oligonucleotide and a P2'oligonucleotide, the P2 oligonucleotide having a 3' end subjected to an extension inhibition treatment, which has an identity of at least 80% with respect to a base sequence including at least the 104th to the 123rd bases of the base sequence indicated in SEQ ID NO: 1 and has a length of from 20 to 80 bases; and the P2' oligonucleotide having a 3' end subjected to an extension inhibition treatment, which hybridizes under stringent conditions with a complementary strand of a base sequence including at least the 104th to 123rd bases of the base sequence indicated in SEQ ID NO: 1 and having a length of from 20 to 80 bases.

[3] The oligonucleotide for a detection test of a polymorphism according to [1], wherein a base corresponding to the 104th base is at a position of any one of a 1st to a 3rd position from a 5' end of the P2 oligonucleotide or the P2' oligonucleotide.

[4] The oligonucleotide for a detection test of a polymorphism according to [2], wherein a base corresponding to the 104th base is at a 5' end of the P2 oligonucleotide or the P2' oligonucleotide.
[5] The oligonucleotide for a detection test of a polymorphism according to any one of [1] to [4], wherein the oligonucleotide has a length of from 25 to 50 bases.
[6] The oligonucleotide for a detection test of a polymorphism according to any one of [1] to [4], wherein the oligonucleotide has a length of from 26 to 42 bases.
[7] The oligonucleotide for a detection test of a polymorphism according to any one of [1] to [6], wherein the extension inhibition treatment is addition of a phosphate group.
[8] The oligonucleotide for a detection test of a polymorphism according to any one of [1] to [7], wherein the oligonucleotide includes a base labeled with a fluorescent dye.
[9] A method of detecting a polymorphism of EGFR exon 19, the method comprising detecting the polymorphism of EGFR exon 19 using the oligonucleotide for a detection test of a polymorphism according to any one of [1] to [8].
[10] The method of detecting a polymorphism according to [9], wherein the method comprises:
  providing a sample nucleic acid which may contain a single-stranded nucleic acid having the base sequence shown in SEQ ID NO:1;
  contacting the oligonucleotide for a detection test of a polymorphism and the single-stranded nucleic acid to obtain a hybrid containing the oligonucleotide for a detection test of a polymorphism and the single-stranded nucleic acid to inhibit an amplification of the single-stranded nucleic acid; and
  carrying out a nucleic acid amplification for the sample nucleic acid at the time of or after the contact between the oligonucleotide for a detection test of a polymorphism and the single-stranded nucleic acid.
[11] The method of detecting a polymorphism according to [10], wherein the nucleic acid amplification is carried out in the presence of a probe that is hybridizable to a nucleic acid having a polymorphic site in the target EGFR exon 19.
[12] The method of detecting a polymorphism according to [11], wherein the probe has an identity of 45% or higher with respect to the base sequence of the oligonucleotide for a detection test of a polymorphism.
[13] The method of detecting a polymorphism according to [11] or [12], wherein the probe emits fluorescence when not hybridized with a target sequence thereof, and a fluorescence intensity decreases when the probe hybridizes with the target sequence thereof.
[14] A method of evaluating a drug efficacy of or tolerance to an EGFR tyrosine kinase inhibitor, the method comprising:
  detecting a polymorphism in EGFR exon 19 by the method of detecting a polymorphism according to any one of [9] to [13]; and
  evaluating tolerance to the EGFR tyrosine kinase inhibitor or efficacy of the EGFR tyrosine kinase inhibitor based on a result of the detection.
[15] A reagent kit for a detection test of a polymorphism of EGFR, comprising at least one oligonucleotide for a detection test of a polymorphism according to any one of [1] to [8].
[16] The reagent kit for a detection test of a polymorphism of EGFR according to [15], further comprising a probe that is hybridizable to a nucleic acid sequence including a target polymorphic site in the EGFR exon 19.
[17] The reagent kit for a detection test of a polymorphism of EGFR according to [16], wherein the probe has an identity of not less than 45% with respect to the base sequence of the oligonucleotide for a detection test of a polymorphism.
[18] The reagent kit for a detection test of a polymorphism of EGFR according to any one of [15] to [17], further comprising a primer set that can amplify a nucleic acid sequence having a target polymorphic site of the EGFR 19.

BRIEF DESCRIPTION OF THE DRAWINGS

FIG. 4A shows the differential melting curve of the sample of Example 3 according to the present invention.
FIG. 4B shows the differential melting curve of the sample of Example 3 according to the present invention.
FIG. 4C shows the differential melting curve of the sample of Example 3 according to the present invention.
FIG. 4D shows the differential melting curve of the sample of Example 3 according to the present invention.
FIG. 5A shows the differential melting curve of the sample of Comparative Example 1 according to the present invention.
FIG. 5B shows the differential melting curve of the sample of Comparative Example 1 according to the present invention.
FIG. 5C shows the differential melting curve of the sample of Comparative Example 1 according to the present invention.
FIG. 5D shows the differential melting curve of the sample of Comparative Example 1 according to the present invention.
FIG. 6A shows the differential melting curve of the sample of Comparative Example 2 according to the present invention.
FIG. 6B shows the differential melting curve of the sample of Comparative Example 2 according to the present invention.

FIG. 9A shows the differential melting curve of the sample A of Example 4 according to the present invention.

FIG. 9B shows the differential melting curve of the sample B of Example 4 according to the present invention.

FIG. 9C shows the differential melting curve of the sample C of Example 4 according to the present invention.

FIG. 9D shows the differential melting curve of the sample D of Example 4 according to the present invention.

FIG. 9E shows the differential melting curve of the sample E of Example 4 according to the present invention.

FIG. 10A shows the differential melting curve of the sample F of Example 4 according to the present invention.

FIG. 10B shows the differential melting curve of the sample G of Example 4 according to the present invention.

FIG. 10C shows the differential melting curve of the sample H of Example 4 according to the present invention.

FIG. 10D shows the differential melting curve of the sample I of Example 4 according to the present invention.

FIG. 10E shows the differential melting curve of a sample J of Example 4 according to the present invention.

DETAILED DESCRIPTION OF THE INVENTION

Figure 1A:
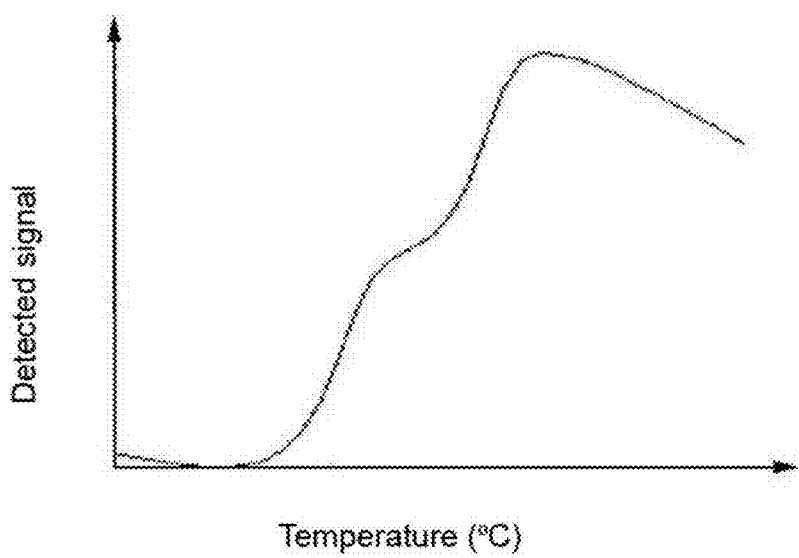
FIG. 1A shows an example of a melting curve of a nucleic acid mixture.

The oligonucleotide for a detection test of a polymorphism of EGFR exon 19 according to the present invention (hereinafter also referred to as simply "oligonucleotide for polymorphism detection test") is an oligonucleotide having a 3' end subjected to an extension inhibition treatment, which is a homologous sequence to and the same length as a base sequence having a length of from 9 to 80 bases and including at least the 115th to the 123rd bases of the base sequence indicated in SEQ ID NO: 1, that is, the oligonucleotide for a detection test of a polymorphism of EGFR exon 19 according to the present invention is at least one selected from the group consisting of a P1 oligonucleotide and a P1' oligonucleotide, the P1 oligonucleotide having a 3' end subjected to an extension inhibition treatment, which has an identity of at least 80% with respect to a base sequence including at least the 115th to the 123rd bases of the base sequence indicated in SEQ ID NO: 1 and has a length of from 9 to 80 bases shown in; and, the P1' oligonucleotide having a 3' end subjected to an extension inhibition treatment, which hybridizes under stringent conditions with a complementary strand of a base sequence including the 115th to the 123rd bases of the base sequence indicated in SEQ ID NO: 1 and having a length of from 9 to 80 bases.

The reagent kit for a polymorphism detection test according to the present invention is a kit which contains the oligonucleotide for a detection test of a polymorphism of EGFR exon 19.

The method of detecting a polymorphism of EGFR gene according to the present invention is a method which includes detecting the polymorphism of EGFR exon 19 using at least one oligonucleotide for a detection test of a polymorphism of EGFR exon 19.

The method of evaluating drug efficacy of an EGFR tyrosine kinase inhibitor is a method which includes detecting a polymorphism in EGFR exon 19 by the method of detecting a polymorphism; and evaluating the tolerance to an EGFR tyrosine kinase inhibitor or efficacy of an EGFR tyrosine kinase inhibitor based on the result of the detection.

According to the present invention, an oligonucleotide, which has a base sequence having the same length as that of a certain part of the EGFR gene indicated in SEQ ID NO: 1 and being homologous to the base sequence of the certain part, that is, which has a base sequence having an identity of at least 80% and/or is hybridizable to a complementary strand of the certain part of the base sequence under stringent conditions, and having a 3' end subjected to an extension inhibition, has a high affinity for the certain part of the base sequence of a wild-type EGFR exon 19 which may contain a polymorphism. The oligonucleotide thus preferentially and strongly hybridizes with the nucleic acid of a wild-type EGFR exon 19 compared to that of a mutant-type EGFR exon 19. Since the 3' end of the oligonucleotide has been subjected to an extension inhibition, the oligonucleotide for a detection test of a polymorphism is not extended even if a DNA polymerase is applied to the oligonucleotide after hybridizing to the nucleic acid of a wild-type EGFR.

The oligonucleotide for a detection test of a polymorphism is an oligonucleotide preferably used for a detection test of a polymorphism in EGFR exon 19. When used for a detection test of a polymorphism in an EGFR, the oligonucleotide for a detection test of a polymorphism hybridizes with the nucleic acid of a wild-type EGFR gene due to the high similarity between the two base sequences. When subjected to a treatment such as nucleic acid amplification under the circumstances where the nucleic acid of a wild-type EGFR gene hybridized with the oligonucleotide and a mutant-type (polymorphism) EGFR gene having deletions or single nucleotide polymorphisms in a region corresponding to the region hybridized with the oligonucleotide co-exist, the amplification of a nucleic acid sequence of a wild-type gene is inhibited by the oligonucleotide for a detection test of a polymorphism. However, the nucleic acid amplification of the mutant-type EGFR gene is not inhibited because of the nucleic acid sequence of the mutant-type EGFR gene never hybridizing to the oligonucleotide for a detection test of a polymorphism. The nucleic acid sequence of the mutant-type EGFR gene is thus preferentially amplified. Accordingly, a sample contains more nucleic acid sequence of the mutant-type EGFR gene than that of the wild-type EGFR gene, and a polymorphism of the EGFR exon 19 can be sensitively detected. The nucleic acid of the wild-type EGFR gene with which the oligonucleotide for a detection test of a polymorphism can hybridize is that with a base sequence complimentary to the base sequence indicated in SEQ ID NO: 1.

According to the present invention, such convenient and sensitive detection of a polymorphism of EGFR exon 19 allows for convenient and sensitive evaluation of tolerance of an EGFR tyrosine kinase inhibitor or efficacy of an EGFR tyrosine kinase inhibitor based on the polymorphism.

The term "EGFR gene" as used herein refers to, in particular, EGFR exon 19. EGFR exon 19 in the present invention has been well-known, and the base sequence thereof refers to a sequence from bases 4831717 to 4832003 of NCBI accession no. NT_033968 (NT_033968.6). The base sequence of SEQ ID NO: 1 corresponds to a part of the base sequence of the nucleic acid of EGFR exon 19.

The region of the base sequence of a wild-type EGFR gene hybridizable to the oligonucleotide for a detection test of a polymorphism is specifically referred to herein as an "amplification inhibition target region".

The polymorphism of the EGFR gene to be detected herein includes a polymorphism having a deletion of a region composed of successive bases in the base sequence corresponding to the base sequence of a wild-type EGFR gene, also may encompass a polymorphism with one base deletion or a polymorphism in which one or two or more bases are successionally replaced by other bases as long as the polymorphism can be detected, and further may contain concurrently two or more polymorphisms as long as an amplification inhibition target region is contained in part of the EGFR gene.

The term "detection test of a polymorphism" as used herein refers to a test used for detecting a polymorphism of a certain gene, and refers to any act for judging whether or not a nucleic acid contains a mutant-type EGFR gene having a polymorphism in the nucleic acid sample, regardless of expressions such as test, assay, detection method, assessment method, or evaluation method.

In the present invention, the descriptions of the base sequences of the sample nucleic acid in a sample to be detected, the oligonucleotide for detection test of a polymorphism, the probe and the primer also apply to complementary base sequences thereof, respectively, unless otherwise specified. Further, when the description of a particular base sequence is applied to a complementary base sequence thereof, descriptions of base sequences recognized by the particular base sequence in the present invention should be applied provided that the recognition by the particular base sequence should be replaced with recognition by a complementary base sequence of the particular base sequence, within a range of the common general technical knowledge of those skilled in the art.

The term "a template nucleic acid sequence" as used herein refers to a base sequence which a primer recognizes and anneals to as a template upon nucleic acid amplification.

In the present invention, the term "Tm value" is defined as a temperature at which a double-stranded nucleic acid dissociates (dissociation temperature: Tm), and is generally defined as a temperature at which the absorbance at 260 nm has increased by 50% of the total increase in absorbance resulting from complete dissociation of the double-stranded nucleic acid. More specifically, when a solution containing a double-stranded nucleic acid such as a double-stranded DNA is heated, the absorbance at 260 nm of the double-stranded nucleic acid gradually increases. This is because the hydrogen bonds between both strands of the double-stranded DNA are broken by heating, thereby dissociating the double-stranded DNA into single-stranded DNAs (melting of DNA). When the double-stranded DNA has completely dissociated into single-stranded DNAs, the single-stranded DNAs exhibit an absorbance that is about 1.5 times the absorbance at the time of the initiation of the heating (i.e., the absorbance when the entire DNA is in the form of a double-stranded DNA), which serves as an indicator of the completion of the melting. The Tm value is defined based on this phenomenon.

In the present invention, when the phrase "the first to third bases from the 3' end" is used in connection to an oligonucleotide sequence, it is assumed that the base at the 3' end of the oligonucleotide chain is the first base from the 3' end. Similarly, when the phrase "the first to third bases from the 5' end" is used in connection to an oligonucleotide sequence, it is assumed that the base at the 5' end of the oligonucleotide chain is the first base from the 5' end.

In the present specification, the scope of the term "process" includes not only a discrete process, but also a process that cannot be clearly distinguished from another process as long as the expected effect of the process of interest is achieved.

In the present specification, any numerical range expressed using "to" refers to a range including the numerical values before and after "to" as the minimum and maximum values, respectively.

In a case in which the amount of a component that may be included in the composition is indicated in the present invention, when there are plural substances corresponding to the component in the composition, the indicated amount means the total amount of the plural substances present in the composition, unless specifically stated otherwise.

The present invention is described below.

<Oligonucleotide for Detection Test of Polymorphism>

The oligonucleotide for a detection test of a polymorphism is at least one oligonucleotide for a detection test of a polymorphism in EGFR exon 19 selected from the group consisting of the following P1 oligonucleotide and P1' oligonucleotide:

the P1 oligonucleotide having a 3' end subjected to an extension inhibition treatment, which has an identity of at least 80% with respect to a base sequence including at least the 115th to the 123rd bases of the base sequence indicated in SEQ ID NO: 1 and has a length of from 9 to 80 bases; and the P1' oligonucleotide having a 3' end subjected to an extension inhibition treatment, which hybridizes under stringent conditions with a complementary strand of a base sequence including the 115th to the 123rd bases of the base sequence indicated in SEQ ID NO: 1 and has a length of from 9 to 80 bases.

It is necessary that the oligonucleotide for a detection test of a polymorphism has a sequence which an identity at least 80% with respect to a base sequence of a defined region containing at least the 115th to the 123rd bases of the base sequence indicated in SEQ ID NO: 1, or a sequence which hybridizes under stringent conditions with a complementary strand of the base sequence in the defined region. It becomes possible to sensitively detect a polymorphism having, for example, one or more base deletions in the base sequence of the 115th or latter bases indicated in SEQ ID NO: 1 since the base sequence from the 115th to the 123rd bases is contained in the oligonucleotide. The 115th base in the sequence indicated in SEQ ID NO: 1 corresponds to a base which is a 3'-flanking base of the 744th codon of EGFR exon 19.

It is necessary that the identity of the P1 oligonucleotide to the defined region of the base sequence is at least 80%. Alternatively, from the viewpoint of detection sensitivity, the P1 oligonucleotide may have an identity of 85% or higher, an identity of 90% or higher, an identity of 95% or higher, an identity of 96% or higher, an identity of 97% or higher, an identity of 98% or higher, or an identity of 99% or higher.

The P1' oligonucleotide is a base sequence hybridizing with the complimentary strand of the defined region of the base sequence indicated in SEQ ID NO: 1 under stringent conditions.

The hybridization may be carried out according to a known method or a method corresponding thereto, such as a method described in Molecular Cloning 3rd (J. Sambrook et al., Cold Spring Harbor Lab. Press, 2001). This document is incorporated herein by reference.

The term "stringent condition" means a condition in which specific hybridization occurs to form a hybrid whereas non-specific hybridization does not occur. A typical stringent condition is, for example, a condition in which hybridization is carried out at a potassium concentration of from about 25 mM to about 50 mM and a magnesium concentration of from about 1.0 mM to about 5.0 mM. One example of the condition in the present invention is a condition in which hybridization is carried out in Tris-HCl (pH 8.6) at 25 mM KCl and 1.5 mM MgCl$_2$; however, the condition in the present invention is not limited thereto. Another example of the stringent condition is described in Molecular Cloning 3rd (J. Sambrook et al., Cold Spring Harbor Lab. Press, 2001). This document is incorporated herein by reference. Those skilled in the art can readily choose such a condition by changing the hybridization reaction, the salt concentration of the hybridization reaction solution, and the like.

The P1 or P1' oligonucleotide in the present invention encompasses an oligonucleotide having a sequence wherein in a base(s) have been inserted to, deleted from and/or substituted in the P1 or P1' oligonucleotide.

The oligonucleotide for a detection test of a polymorphism having a sequence wherein a base(s) have been inserted, deleted and/or substituted is not particularly limited, as long as the oligonucleotide exhibits an effect similar to that of the P1 or P1' oligonucleotide; and, in cases where a base(s) have been inserted, deleted and/or substituted, the position(s) of the insertion(s), deletion(s) and/or substitution(s) are not particularly limited. The number of bases that have been inserted, deleted, and/or substituted may be, for example, 1 base, or 2 or more bases, such as from 1 base to 10 bases, from 1 base to 5 bases and from 1 base to 3 bases, although varying depending on the total length of the oligonucleotide for a detection test of a polymorphism.

The position of the first base of the oligonucleotide for a detection test of a polymorphism is not limited to the 115th base of SEQ ID NO: 1, and may be a base at any position of the 60th to the 115th bases, the 100th to the 110th bases, or the 102nd to the 106th bases of the base sequence indicated in SEQ ID NO: 1.

It is necessary that the length of the oligonucleotide for a detection test of a polymorphism is from 9 mer to 80 mer so as to be equal to the length of from 9 mer to 80 mer of the base sequence containing at least the base sequence from the 115th to the 123rd bases in the base sequence indicated in SEQ ID NO: 1. An oligonucleotide for a detection test of a polymorphism with a length of not more than 8 mer or not less than 81 mer may never achieve the intended detection sensitivity. The oligonucleotide for a detection test of a polymorphism may have a length of from 20 mer to 80 mer, from 10 mer to 70 mer, from 25 mer to 50 mer, or from 26 mer to 42 mer. Among them, a shorter oligonucleotide for a detection test of a polymorphism tends to, for example, more completely inhibit nucleic acid amplification of the wild-type nucleic acid, and thereby the detection sensitivity is improved.

Examples of such an oligonucleotide for a detection test of a polymorphism include an oligonucleotide having a length of from 10 mer to 80 mer, whose first nucleotide corresponds to any one base from the 60th to the 115th bases indicated in SEQ ID NO: 1, an oligonucleotide having a length of from 25 mer to 50 mer, whose first nucleotide corresponds to any one base from the 100th to the 110th bases, and an oligonucleotide having a length of from 26 mer to 42 mer, whose first nucleotide corresponds to any one base from the 102nd to the 106th bases. Such oligonucleotides tend to, for example, more completely inhibit the nucleic acid amplification of the wild-type nucleic acid, and thereby the detection sensitivity is improved.

Example of such an oligonucleotide for a detection test of a polymorphism may include at least one selected from the group consisting of the following P2 oligonucleotide and P2' oligonucleotide:

the P2 oligonucleotide having a 3' end subjected to an extension inhibition treatment, which has an identity of at least 80% with respect to a base sequence including at least the 104th to the 123rd bases of the base sequence indicated in SEQ ID NO: 1 and has a length of from 20 to 80 bases and, the P2' oligonucleotide having a 3' end subjected to an extension inhibition treatment, which hybridizes under stringent conditions with a complementary strand of a base sequence including at least the 104th to the 123rd bases of the base sequence indicated in SEQ ID NO: 1 and has a length of from 20 to 80 bases.

In the P2 or P2' oligonucleotide, the first base in the oligonucleotide may corresponded to any base of the base sequence indicated in SEQ ID NO: 1 as long as the base sequence of the P2 or P2' oligonucleotide is a base sequence having a length of from 20 mer to 80 mer and including the 104th to the 123rd bases of the base sequence indicated in SEQ ID NO: 1. For example, the P2 or P2' oligonucleotide may have the 104th base located in a position of the base sequence from the 1st to the 3rd base from the 5' end, and further may have the 104th base located at the 5' end side, i.e., in a position of the first base of the P2 or P2' oligonucleotide. The oligonucleotide in which the 104th base of SEQ ID NO: 1 is located in a position of the base sequence from the 1st to the 3rd base from the 3' end, particularly at the 3' end allows, for example, more complete inhibition of nucleic acid amplification of the wild-type nucleic acid.

The stringent conditions applied for the P2' oligonucleotide are the same as those in the P1' oligonucleotide.

The P2 or P2' oligonucleotide according to the present invention further encompasses oligonucleotides with one or two or more bases inserted, deleted, or substituted in each oligonucleotide.

The description for one or more nucleotides inserted to, deleted from, or substituted to the base sequence of the P2 or P2' oligonucleotide is the same as that in the P1 or P1' oligonucleotide.

The oligonucleotide for detection test of polymorphism may be also labeled for detecting the oligonucleotide for detection test of polymorphism or a complementary strand thereof.

Examples of labeled substances provided to the oligonucleotide for a detection test of a polymorphism generally include fluorescent dyes and fluorophores. A labeled substance is generally provided to oligonucleotide bases, but the invention is not limited this. The bases with the labeled substance may be any base of the oligonucleotide for a detection test of a polymorphism, and be located anywhere in the oligonucleotide. Labeling of the bases located anywhere in the oligonucleotide for a detection test of a polymorphism with a fluorescent dye advantageously allows for efficiently detecting the presence or absence of the nucleic acid hybridized with the oligonucleotide for a detection test of a polymorphism.

It is necessary that the 3' end of the oligonucleotide for a detection test of a polymorphism has been subjected to an extension inhibition treatment. The term "extension" as used herein refers to extension of a nucleotide chain by nucleic acid amplification with enzymes such as a DNA or RNA polymerase. The extension inhibition treatment is not specifically limited as long as it is a treatment in which extension from the 5' end to the 3' end of an oligonucleotide chain is inhibited. For example, addition of a substituent(s) or a compound(s) to the nucleic acid at the 3' end side of an oligonucleotide chain is included.

Examples of a substituent to be added for such extension inhibition include a phosphate group and a ddNTP group. Examples of compounds to be added for extension inhibition include fluorescent dyes; 2',3'-ddA, 2',3'-ddC; 2',3'-ddG; and 2',3'-ddT. In the extension inhibition of an oligonucleotide chain, a phosphate group may be added to the nucleic acid at the 3' end from the viewpoint of, for example, complete extension inhibition. The location of the nucleic acid having the substituent or compound thereon may be varied depending on means used for the nucleic acid extension. When using a DNA or RNA polymerase, the location is not limited, and may be at the 3 position of (deoxy)ribose.

The oligonucleotide for a detection test of a polymorphism may include a base labeled with a fluorescent dye on the base sequence thereof.

Examples of the fluorescent dyes include, but not specifically limited to, fluorescein, phosphors, rhodamine, and polymethine pigment derivatives. Commercially available are BODIPY FL, Pacific Blue, FluorePrime, Fluoredite, FAM, Cy3 and Cy5, TAMRA, and the like.

Some examples of oligonucleotides for a detection test of a polymorphism according to the present invention will be described below. In the Table, the mark "(P)" represents a phosphate group. For each base sequence indicated in SEQ ID NO: 1, Cmp-1 represents a 40-mer oligonucleotide starting from the 104th base, Cmp-2 represents a 29-mer oligonucleotide starting from the 104th base, Cmp-3 represents a 28-mer oligonucleotide starting from the 115th base, Cmp-4 represents a 49-mer oligonucleotide starting from the 89th base, Cmp-5 represents a 47-mer oligonucleotide starting from the 79th base, Cmp-6 represents a 36-mer oligonucleotide starting from the 107th base, Cmp-7 represents a 20-mer oligonucleotide starting from the 104th base, Cmp-8 represents a 80-mer oligonucleotide starting from the 104th base, Cmp-9 represents a 80-mer oligonucleotide starting from the 63rd base, Cmp-10 represents a 39-mer oligonucleotide starting from the 105th base, Cmp-11 represents a 38-mer oligonucleotide starting from the 106th base, Cmp-12 represents a 33-mer oligonucleotide starting from the 111th base, Cmp-13 represents a 29-mer oligonucleotide starting from the 115th base, Cmp-14 represents a 10-mer oligonucleotide starting from the 115th base, and Cmp-15 represents a 78-mer oligonucleotide starting from the 106th base.

TABLE 1

| | sequence (5'→3') | mer | SEQ ID No. |
|---|---|---|---|
| Cmp-1 | CCCGTCGCTATCAAGGAATTAAGAGAAGCAACATCTCCGA-(P) | 40 | 2 |
| Cmp-2 | CCCGTCGCTATCAAGTAATTAAGAGAAGC-(P) | 29 | 3 |
| Cmp-3 | CAAGGAATTAAGAGAAGCAACATCTCCG-(P) | 28 | 4 |
| Cmp-4 | GAGAAAGTTAAAATTCCCGTCGCTATCAAGGAATTCCGAGAAGCAACAT-(P) | 49 | 5 |
| Cmp-5 | CCCAGAAGGTGAGAAAGTTAAAATTCCCGTCGCTATCAAGGAATTAA-(P) | 47 | 6 |
| Cmp-6 | GTCGCTATCAAGGAATTAAGAGAAGCAACATCTCCG-(P) | 36 | 7 |
| Cmp-7 | CCCGTCGCTATCAAGGAATT-(P) | 20 | 8 |
| Cmp-8 | CCCGTCGCTATCAAGGAATTAAGAGAAGCAACATCTCCGAAAGCCAACAAGGAAATCCTCGATGTGAGTTTCTGCTTTGC-(P) | 80 | 9 |
| Cmp-9 | CATAGGGACTCTGGATCCCAGAAGGTGAGAAAGTTAAAATTCCCGTCGCTATCAAGGAATTAAGAGAAGCAACATCTCCG-(P) | 80 | 10 |
| Cmp-10 | CCGTCGCTATCAAGGAATTAAGAGAAGCAACATCTCCGA-(P) | 39 | 11 |
| Cmp-11 | CGTCGCTATCAAGGAATTAAGAGAAGCAACATCTCCGA-(P) | 38 | 12 |
| Cmp-12 | CTATCAAGGAATTAAGAGAAGCAACATCTCCGA-(P) | 33 | 13 |
| Cmp-13 | CAAGGAATTAAGAGAAGCAACATCTCCGA-(P) | 29 | 14 |
| Cmp-14 | CAAGGAATTA-(P) | 10 | 15 |
| Cmp-15 | CGTCGCTATCAAGGAATTAAGAGAAGCAACATCTCCGAAAGCCAACAAGGAAATCCTCGATGTGAGTTTCTGCTTTGC-(P) | 78 | 16 |

Examples of mutants (polymorphism) of EGFR gene detected by the above oligonucleotide for a detection test of a polymorphism include a polymorphism with one or more bases deleted from the region of the base sequence including the base sequence from the 115th to the 123rd bases in the base sequence indicated in SEQ ID NO: 1. For such mutant-type EGFR genes, examples are not limited and will be described below. In Table 2, a mark "–" represents a deletion site, a small letter represents a mutation site, a mark "WT" represents a wild-type EGFR exon 19 (from the 104th to the 151st bases of SEQ ID NO: 1), and a bold underlining "G" in the base sequence of the wild-type gene represents a substitution site.

TABLE 2

| No. | | | SEQ ID No. |
|---|---|---|---|
| WT | Wild Type | CCCGTCGCTATCAAGGAATTAAGAGAAGCAACATCTCCGAAAGCCAAC | 17 |
| 2 | E746_A750del | GCCGTCGCTATCAA---------------AACATCTCCGAAAGCCAAC | 18 |

TABLE 2 -continued

| No. | | | SEQ ID No. |
|---|---|---|---|
| 3 | E746_A750del | GCCGTCGCTATCAAG---------------ACATCTCCGAAAGCCAAC | 19 |
| 4 | L747_E749del, A750P | GCCGTCGCTATCAAGGAA----------CAACATCTCCGAAAGCCAAC | 20 |
| 5 | L747-T751del | GCCGTCGCTATCAAGGAAT---------------CTCCGAAAGCCAAC | 21 |
| 6 | L747_S752del, P753S | GCCGTCGCTATCAAGGAAT-----------------CGAAAGCCAAC | 22 |
| 7 | L747-A750del P ins | GCCGTCGCTATCAAGGAA------------cCATCTCCGAAAGCCAAC | 23 |
| 8 | L747-S752 del S ins | GCCGTCGCTATCAAGGAA-----------------CCGAAAGCCAAC | 24 |
| 9 | E746-T751 del V ins | GCCGTCGCTATCAAGG------------------tTCCGAAAGCCAAC | 25 |
| 10 | L747-A750del | GCCGTCGCTATCAAGGAAT------------CATCTCCGAAAGCCAAC | 26 |
| 12 | L747-S752 del Q ins | GCCGTCGCTATCAAGGAA-----------------CaGAAAGCCAAC | 27 |
| 13 | E747-S752 del V ins | GCCGTCGCTATCAAGG--------------tATCTCCGAAAGCCAAC | 28 |
| 14 | L747_S752del, E746 V | GCCGTCGCTATCAAGGt-----------------TCCGAAAGCCAAC | 29 |
| 15 | E746-A750 del V ins | GCCGTCGCTATCAA-----------------AatTCCGAAAGCCAAC | 30 |
| 17 | L747-E749, T751-S752 del | GCCGTCGCTATCAAGGAA----------CAA-----CCGAAAGCCAAC | 31 |

<EGFR Polymorphism Detection Probe>

In the following method for detecting a polymorphism of EGFR exon 19, a polymorphism detection probe for detecting a polymorphism of EGFR exon 19 (hereinafter referred to as just "polymorphism detection probe") serving as a detection target is used.

The polymorphism detection probe may be capable of detecting a polymorphism having mutations in the position corresponding to an amplification inhibition target site of the oligonucleotide for a detection test of a polymorphism, or may be capable of detecting a polymorphism having a deletion at the position corresponding to an amplification inhibition target site.

Such a polymorphism detection probe particularly may have a base sequence capable of hybridizing with the complementary nucleic acid of a base sequence containing the 115th to the 123rd bases of the base sequence indicated in SEQ ID NO: 1, which may be referred to as the "target sequence" in some cases.

The length of the probe may be, but not limited to, from 5 mer to 50 mer, or from 10 mer to 30 mer. Within the range of the probe length, the detection sensitivity tends to be higher.

The polymorphism detection probe may have an identity of 45% or higher to the base sequence of an oligonucleotide for detecting a polymorphism, and thereby the sensitivity for detecting nucleic acids of a sample containing, for example, a mutant-type EGFR gene can be improved. The polymorphism detection probe may further have an identity of 55% or higher, 65% or higher, or 80% or higher.

The base sequence of the polymorphism detection probe is not particularly limited but including bases corresponding to bases in the 5' end side of mutation (for example, deletion) site to be detected. In the base sequence of the polymorphism detection probe, the bases corresponding to a mutation (deletion) site to be detected may be located at any positions from the 5th or later bases, or from the 10th or later bases counting from the 5' end of the probe, and thereby the detection sensitivity may be improved.

The base sequence of the polymorphism detection probe may also correspond to the base sequence of the wild-type EGFR exon 19, and further include mutations. The polymorphism detection probe may be an oligonucleotide having an identity of from 70% to 100%, or from 80% to 100% to the base sequence indicated in SEQ ID NO: 1 or the complementary base sequence to that base sequence. By making the sequence of the polymorphism detection probe bases corresponding to the wild type, the sensitivity of the detection may be improved.

The polymorphism detection probe may also be an oligonucleotide hybridizing under stringent conditions with the base sequence indicated in SEQ ID NO: 1 or the complementary base sequence, and may be an oligonucleotide having one or more bases insertion, deletion, or substitution.

As the stringent conditions, conditions similar to the conditions described in the section regarding the oligonucleotide for a detection test of a polymorphism may be applied. The range of the identity, and an insertion, a deletion and/or a substitution to be applied may also be similar to those as described in the section regarding the oligonucleotide for a detection test of a polymorphism.

In a case of using the polymorphism detection probe together with a primer in the amplification process of the polymorphism detection probe, the polymorphism detection probe may have the 3' end sequence with a fluorescent label in order to prevent itself from being extended by DNA polymerase reaction directed to the polymorphism detection probe. The polymorphism detection probe may further have the 3' end sequence having a phosphate group therein.

The polymorphism detection probe may be a labeled probe having a label thereon from the viewpoint of detection efficiency.

Specific examples of the labeled substance used for labeled probe include fluorescent dyes and fluorophor.

The polymorphism detection probe may be a fluorescent-labeled oligonucleotide such that the fluorescence intensity when the oligonucleotide is hybridized with a target sequence thereof is decreased (quenched) or increased as compared to the fluorescence intensity when the oligonucleotide is not hybridized with the target sequence thereof. In particular, the fluorescent-labeled oligonucleotide may be a fluorescent-labeled oligonucleotide such that the fluorescence intensity when the oligonucleotide is hybridized with the target sequence thereof is decreased as compared to the fluorescence intensity when the oligonucleotide is not hybridized with the target sequence thereof.

A probe that utilizes a "fluorescence quenching phenomenon" as described above is generally referred to as guanine quenching probe, and known as Q PROBE®. In particular, the fluorescent-labeled oligonucleotide may be an oligonucleotide designed to have cytosine (C) at its 3' or 5' end, and labeled with a fluorescent dye such that fluorescence emission thereof is reduced when the terminal C approaches guanine (G).

By using such a probe, the hybridization and dissociation of the probe may be readily checked by the change in its signal.

A known detection method other than the detection method using a Q PROBE® may also be applied. Examples of such a detection method include a TAQ-MAN probe method, a a hybridization probe method, a molecular beacon method, and a MGB probe method.

The fluorescent dye is not particularly limited, and examples of the fluorescent dye include fluorescein, phosphor, rhodamine and polymethine dye derivatives. Examples of commercially available products of such fluorescent dyes include Pacific Blue, BODIPY FL, FluorePrime, Fluoredite, FAM, Cy3 and Cy5, and TAMRA.

The detection conditions of the fluorescent-labeled oligonucleotide are not particularly limited, and may be decided, as appropriate, in accordance with the fluorescent dye to be used. For example, Pacific Blue can be detected at a detection wavelength of from 445 nm to 480 nm, TAMRA can be detected at a detection wavelength of from 585 nm to 700 nm, and BODIPY FL can be detected at a detection wavelength of from 520 nm to 555 nm. By using a probe having such a fluorescent dye, hybridization and dissociation of the probe can be readily confirmed based on a change in fluorescence signal thereof. Attachment of a fluorescent dye to the oligonucleotide may be carried out according to an ordinary method, such as a method described in JP-A No. 2002-119291.

In the polymorphism detection probe labeled by a labeled substance such as fluorescent dyes, an unlabeled probe which has the same base sequence as that of the labeled probe may be used together with the labeled probe to adjust signal intensity such as fluorescence intensity to be detected. Alternatively, the unlabeled probe may have, for example, a phosphate group added to its 3' end.

<Primer>

In the below-described method of detecting a polymorphism of EGFR gene, primers are used in a case in which the sequence containing a target sequence containing a polymorphism of EGFR gene mutation to be detected is amplified by a PCR method.

The primers that may be used in a nucleic acid amplification are not particularly limited as long as the primers are capable of amplifying a nucleic acid containing a site of a polymorphism of the EGFR gene of interest to be deleted (for example, a sequence indicated in SEQ ID NO:1 corresponding to a region of a base that has been deleted).

Those skilled in the art are able to design such primers, as appropriate, based on the base sequence indicated in SEQ ID NO: 1.

The length and the Tm value of each primer may be a length of from 12 mer to 40 mer and a Tm of from 40° C. to 70° C., or a length of from 16 mer to 30 mer and a Tm of from 55° C. to 60° C.

The length of each primer in the primer set does not have to be the same as each other, and the Tm values of both primers of the primer set may be substantially the same (or the difference between the Tm values of both primers may be within 5° C.).

<Method of Detecting Polymorphism of EGFR Gene>

The method of detecting a polymorphism of EGFR exon 19 according to the present invention is a method including detecting a polymorphism of EGFR exon 19 using at least one oligonucleotide for detecting a polymorphism.

According to the detection method, at least one oligonucleotide for a detection test of a polymorphism preferentially hybridizes with a wild-type EGFR gene to conveniently distinguish between the wild-type EGFR gene and the mutant-type EGFR gene, and thereby a mutant-type EGFR gene can be sensitively detected.

The method of detecting a polymorphism of EGFR exon 19 is not particularly limited as long as it is a method utilizing the fact the oligonucleotide for a detection test of a polymorphism of the present invention preferentially hybridizes with a nucleic acid of a wild-type EGFR gene compared to a nucleic acid of a mutant-type EGFR gene.

Such a detection method may include, for example, a method including nucleic acid amplification. In the method including the nucleic acid amplification, the base sequence of the polymorphism detection probe preferentially hybridizes with a nucleic acid of a wild-type EGFR gene, and thereby the amplification of the nucleic acid of the wild-type EGFR gene is inhibited. The mutant-type EGFR gene nucleic acid may thus be preferentially amplified.

Particularly, the method of detecting a polymorphism of EGFR exon 19 may be a polymorphism detection method including: providing a sample nucleic acid which may contain a single-stranded nucleic acid having the base sequence indicated in SEQ ID NO:1 (a nucleic acid sample preparation process); contacting the oligonucleotide for a detection test of a polymorphism and the single-stranded nucleic acid to obtain a hybrid containing the oligonucleotide for a detection test of a polymorphism and the single-stranded nucleic acid to inhibit an amplification of the single-stranded nucleic acid (a first hybridization process); and carrying out a nucleic acid amplification for the nucleic acid sample at the time of or after the contact between the oligonucleotide for a detection test of a polymorphism and the single-stranded nucleic acid (a nucleic acid amplification process). Such a method of detecting a polymorphism has advantages in that, for example, a polymorphism of EGFR exon 19 can be conveniently and sensitively detected.

Examples of a nucleic acid sample provided in the nucleic acid sample preparation process include, but not specifically limited to, a sample containing a nucleic acid derived from biological samples. Examples of the biological samples include a sample that is derived from or can be derived from any biological source, examples of which include: a tissue such as colon or lung; a hemocyte such as a leukocyte cell; whole blood; plasma; a sputum; a suspension of oral mucosa; a somatic cell of nail, hair or the like; a germ cell; milk; ascitic fluid; a paraffin-embedded tissue; gastric juice; a gastric lavage fluid; urine; peritoneal fluid; amniotic fluid; and a cell culture. The method for sampling the sample, the method for preparing the sample containing a nucleic acid, and the like are not limited, and, conventional methods known in the art may be employed therefor. A nucleic acid obtained from such a biological source may be directly used as the template, or may be used after the sample has been subjected to pretreatment that modifies the properties of the sample. A reaction liquid obtained after the nucleic acid amplification using a nucleic acid derived from a biological sample for a template may be employed as a nucleic acid sample according to the present invention, in which the amplification product is defined as a template nucleic acid sequence.

In the case of whole blood, the isolation of genomic DNA from whole blood may be performed by conventional known methods. For example, used is a commercially available genomic DNA isolation kit (GFX Genomic Blood DNA Purification kit; GE Healthcare Bioscience).

The sample may be any of, for example, a sample which is unclear contains a nucleic acid having a target base site which is not known for whether the mutant type or the normal type, a sample which is readily known as containing both a nucleic acid having the mutant type sequence and a nucleic acid having the normal type sequence, and a sample which possibly contains a nucleic acid having the mutant type sequence or a nucleic acid having the normal type sequence. Origin of nucleic acid in a sample, for example, origin of DNA, RNA, and the like is not limited. Examples thereof include a cell such as various cancer cells, a virus, mitochondria, and the like. In embodiments, the method may be specifically preferably applied to a sample having a nucleic acid of the mutant type and nucleic acid of the normal type. Examples of such sample include a biological sample such as various cancer cells, and specific examples thereof include a lung cancer cell and the like. Since cancer cells in blood include both cells having the mutant type nucleic acid and cells having normal type nucleic acid, the method of detecting a polymorphism of the exemplary embodiment of the present invention may be preferably applied to nucleic acid samples derived from such cells, because the method may achieve required sensitivity. In the present invention, method to collect the samples, method to prepare the nucleic acids, and the like is not limited, and conventional methods well-known in the art may be employed.

The nucleic acid in the sample may be single-stranded or double-stranded. Examples of the nucleic acid sequence in the sample include DNA, and RNA, such as total RNA or mRNA. Examples of the nucleic acid sequence include a nucleic acid contained in a sample such as a biological sample.

A nucleic acid which is contained in the sample may be a nucleic acid originally contained in the biological sample, or alternatively, in view of increasing detectability, it may be an amplicon which is a amplification product made by a nucleic acid amplification method using a nucleic acid in a biological sample as a template. Specific examples include an amplicon made by a nucleic acid amplification method with use of a nucleic acid originally contained in a biological sample as a template, and an amplicon made by a nucleic acid amplification method with use of a cDNA as a template, in which the cDNA is generated from RNA originally contained in the biological sample by reverse transcription-PCR (RT-PCR: Reverse Transcription PCR). These amplicons may be used as template nucleic acids. The length of such amplicon may be, for example, in a range of from 50 bases to 1000 bases, and preferably in a range of from 80 bases to 200 bases, but not limited thereto.

In the first hybridization process, an oligonucleotide for a detection test of a polymorphism is brought into contact with the single-stranded nucleic acid to obtain a hybrid which contains the oligonucleotide for a detection test of a polymorphism and the single-stranded nucleic acid and may inhibit the nucleic acid amplification of the single-stranded nucleic acid. The hybrid is obtained by hybridization between the oligonucleotide for a detection test of a polymorphism and the single-stranded nucleic acid under hybridizable conditions.

With regard to the hybridizable condition in the first hybridization process, a common condition for hybridization between single-stranded nucleic acids may be applied without change. The hybridization condition between a primer and a single-stranded nucleic acid, described below, may thus be applied without change. Thus, the hybrid of the oligonucleotide for a detection test of a polymorphism and the single-stranded nucleic acid having base sequence indicated in SEQ ID NO: 1 is obtained under the hybridizable condition in the first hybridization process. The hybrid obtained in the first hybridization process is a double-stranded nucleic acid of the single-stranded nucleic acid of the sample and the oligonucleotide for a detection test of a polymorphism, the nucleic acid amplification of the nucleic acid sequence forming hybrid structure is inhibited.

The oligonucleotide for a detection test of a polymorphism may be added to a nucleic acid sample such as a liquid sample containing an isolated genomic DNA, or may be mixed with a genomic DNA in an appropriate solvent. The solvent is not particularly limited, and examples of the solvent include conventional solvents known in the art, such as: a buffer solution such as Tris-HCl; a solvent containing at least one of KCl, $MgCl_2$, $MgSO_4$, or glycerol; and a PCR reaction solution.

The condition of contact between the oligonucleotide for a detection test of a polymorphism and the single-stranded nucleic acid of the sample is not particularly limited. For example, the oligonucleotide for a detection test of a polymorphism may be added into a sample including a certain amount of the single-stranded nucleic acid to obtain a desired ratio of an amount of the oligonucleotide for a detection test of a polymorphism and an amount of the single-stranded nucleic acid.

In the first hybridization process, a subject sample preferably contains the oligonucleotide for a detection test of a polymorphism and the polymorphism detection probe. By using the subject sample containing the polymorphism detection probe, there is an advantage in that the detection of a polymorphism of EGFR exon 19 may be carried out, for example, conveniently and sensitively.

In the present invention, the addition ratio of the polymorphism detection probe relative to the nucleic acids in the sample to be detected (or the amplification products containing a sequence to be detected) (in a molar ratio) may be 10 or lower, 5 or lower, or 3 or lower. The lower limit of the ratio is not particularly limited, and may be, for example, 0.0001 or higher, 0.001 or higher, or 0.01 or higher.

The "nucleic acids in the sample" may be, for example, a total of nucleic acids to be detected that have the gene mutation to be detected and nucleic acids, other than the nucleic acids to be detected, that do not have the gene mutation, or a total of amplification products containing a detection target sequence having the gene mutation to be detected and amplification products containing a sequence, other than the detection target sequence, that does not have the gene mutation.

The above-described addition rate of the polymorphism detection probe relative to the subject nucleic acid may be, for example, a molar ratio relative to double stranded nucleic acids or a molar ratio relative to single-stranded nucleic acids.

The amount of the polymorphism detection probe to be added to the reaction system is not particularly limited. For example, the amount of the probe added may be preferably in the range of from 10 nmol to 400 nmol per liter of the reaction system, and more preferably in the range of from 20 nmol to 200 nmol per liter of the reaction system.

In the nucleic acid amplification process, the nucleic acid amplification is carried out with respect to the nucleic acid sample at the time of or after the contact between the oligonucleotide for a detection test of a polymorphism and the nucleic acid sample. The nucleic acid amplification treatment may be carried out after the first hybridization process or approximately at the same time as the first hybridization process as long as the hybrid formation has been almost completed. The single-stranded nucleic acid in the nucleic acid sample, which has not formed a hybrid in the first hybridization step, is thus amplified.

In the amplification, the nucleic acid sample and the primer set are made to contact, and amplification is performed with use of a nucleic acid contained in a sample as a template. In this process, each primer anneals to a template nucleic acid sequence in one sample (one reaction solution), and then amplification of the nucleic acid is started. The template nucleic acid sequence of the present invention comprises a wild-type template nucleic acid sequence containing the amplification inhibition target site.

In the nucleic acid amplification process, a ratio of an addition amount of the nucleic acid sample to an amount of the amplification reaction system (for example, a reaction solution) is not particularly limited. When the nucleic acid sample is a biological sample (for example, whole blood sample), a lower limit of the addition ratio may be 0.01 v/v % or more, 0.05 v/v % or more, or 0.1 v/v % or more. Also, an upper limit of the addition ratio is not particularly limited. It may be 2 v/v % or less, 1 v/v % or less, or 0.5 v/v % or less.

When an optical detection which uses a labeled probe is employed in the detection of mutation which is explained below, a ratio of an addition amount of a biological sample, such as whole blood sample in the reaction, to an amount of the amplification reaction system may be, for example, in a range of from 0.1 w/w % to 0.5 w/w %. In this range, generation of sediment caused by denaturation may be sufficiently suppressed, and sensitivity in an optical method may be increased. Also, inhibition of PCR caused by contaminant in whole blood may also be suppressed, and further increase of amplification efficiency may be expected.

Prior to beginning of the amplification reaction, albumin may be preferably added to the reaction system. By such addition of albumin, for example, influences caused by sediment or turbidity may be further decreased and amplification efficiency may be further increased.

In the reaction system, a ratio of an addition amount of albumin to an amount of the reaction system may be, for example, from 0.01 w/w % to 2 w/w %, from 0.1 w/w % to 1 w/w %, or from 0.2 w/w % to 0.8 w/w %. Examples of the albumin include, but not particularly limited to, bovine serum albumin (BSA), human serum albumin, rat serum albumin, and horse serum albumin. These albumins may be respectively used individually or in a combination of two or more of these.

In the nucleic acid amplification process, the method of amplifying a nucleic acid may be, for example, a method in which a polymerase is employed. Examples of thereof include a Polymerase Chain Reaction (PCR), Isothermal and Chimeric primer-initiated Amplification of Nucleic acids (ICAN) method, Loop-mediated Isothermal Amplification (LAMP) method, Nucleic acid sequence based amplification (NASBA), Transcription-mediated amplification (TMA), Strand Displacement Amplification (SDA), and the like. Conditions of the nucleic acid amplification are not particularly limited, and the nucleic acid amplification can be performed by conventional well-known method in the art.

Amplification in the nucleic acid amplification process is herein explained with PCR as an example, but the invention is not limited thereto. Conditions of the PCR are not particularly limited, and PCR can be performed by conventional well-known method in the art.

Other components of the reaction solution are not particularly limited, and may include conventional-known components. The amounts of the other components are also not particularly limited. Examples of the components include nucleotides such as DNA polymerase, nucleoside triphosphate (dNTP) and solvents thereof. Each component of the reaction solution is added in any order.

The DNA polymerase to be used in the PCR method may be selected, without particular limitation, from DNA polymerases that are usually used for PCR. Examples of the DNA polymerase include GENE TAQ (trade name, manufactured by NIPPON GENE CO., LTD.), PRIMESTAR MAX DNA POLYMERASE (trade name, manufactured by Takara Bio Inc.), and a Taq polymerase.

The amount of the polymerase to be used is not particularly limited as long as a usually-applied polymerase concentration is provided. For example, in a case in which a Taq polymerase is used, the concentration of the Taq polymerase may be, for example, a concentration of from 0.01 U to 10 U relative to 10 μl of the reaction solution, or concentration of from 0.05 U to 1 U relative to 10 μl of the reaction solution. In this range, for example, the affinity for a wild-type nucleic acid of the oligonucleotide for a detection test of a polymorphism tends to be increased.

The PCR method may be carried out under the conditions appropriately selected from usually-employed conditions. Change of a temperature in each step may be, for example, automatically regulated by using thermal cycler or the like.

The method of detecting polymorphism of the present invention may further include a polymorphism evaluation process. The polymorphism evaluation process may include the following processes (I) to (IV), and further include the following process (V).

Process (I): contacting the polymorphism detection probe with a single-stranded nucleic acid in a sample, to obtain a hybrid (second hybridization process).

Process (II): dissociating the hybrid by changing the temperature of the sample containing the hybrid, and measuring a change in fluorescence signal due to the dissociation of the hybrid (a measurement process).

Process (III): measuring a Tm value, which is the dissociation temperature of the hybrid, based on the change in fluorescence signal (Tm value measurement process).

Process (IV): detecting the presence of the polymorphism (gene mutation) of EGFR gene on the single-stranded nucleic acid in the sample, based on the Tm value (polymorphism detection process).

Process (V): determining the abundance ratio of single-stranded nucleic acid having the polymorphism in the total single-stranded nucleic acids contained in the sample, based on the presence of the polymorphism (polymorphism abundance ratio detection process).

Such polymorphism detection method allows convenient and high-sensitive detection in EGFR gene polymorphisms and the evaluation.

Means and conditions of hybridization applied for the second hybridization process are not particularly limited. Conditions for obtaining single-stranded nucleic acids by denaturing double strand nucleic acids and conditions for hybridizing the single-stranded nucleic acid sequences with each other, which are well-known in the art, can be applied as they are.

The heating temperature for dissociation may be, for example, in a range of from 85° C. to 95° C., but not limited thereto as long as the amplified product can be dissociated at the temperature. Usually, duration of heating may be in a range of from 1 sec. to 10 min., or from 1 sec. to 5 min, but not particularly limited thereto. Dissociated single-stranded nucleic acid sequence and a polymorphism detection probe may be hybridized, for example, by lowering the heating temperature after dissociation. Condition for temperature may be, for example, in a range of from 40° C. to 50° C.

Note that the term "single-stranded nucleic acid" related to amplification products herein includes single-stranded nucleic acids originally contained in a nucleic acid sample to be examined.

In the measurement process, the temperature of the sample containing the hybrid is changed for dissociating the hybrid, and a change in fluorescence signal due to the dissociation of the hybrid is measured.

A signal value which indicates dissociation of the hybrid of the single-stranded nucleic acid and the polymorphism detection probe, can be measured with absorbance at a wavelength of 260 nm. Alternatively, it may be measured by measuring a signal which is based on a signal from the label attached to the polymorphism detection probe, and which varies in accordance with the degree of the formation of a hybrid of a single-stranded DNA and the polymorphism detection probe. When measuring of the signal of a labeling substance is employed, for example, detection sensitivity may be increased.

Examples of the labeled probe include a fluorescent-labeled oligonucleotide of which the fluorescence intensity when the oligonucleotide is hybridized with a target sequence thereof is decreased (quenched) as compared to the fluorescence intensity when the oligonucleotide is not hybridized with the target sequence thereof, and a fluorescent-labeled oligonucleotide of which the fluorescence intensity when the oligonucleotide is hybridized with a target sequence thereof is increased as compared to the fluorescence intensity when the oligonucleotide is not hybridized with the target sequence thereof.

The former probe does not show a fluorescence signal or only a weak signal when the probe forms a hybrid (a double-stranded DNA) with the sequence to be detected; and the probe becomes to show a signal or shows an increased signal when the probe is dissociated from the sequence to be detected by heating.

The latter probe shows a signal when the probe forms a hybrid (a double-stranded DNA) with the sequence to be detected; and the probe shows a decreased signal or ceases to show a signal when the probe is dissociated from the sequence to be detected by heating. Therefore, similar to the measurement of the absorbance at 260 nm described above, the progress of melting can be monitored, and the Tm value can be determined by detecting the change in the fluorescence signal from the fluorescent label under the conditions specific to the fluorescent label (for example, the fluorescence wavelength thereof).

Change in the signal based on dissociation of a hybrid is performed by changing temperature of a reaction solution. For example, the reaction solution, that is, the resultant hybrid of the single-stranded DNA and the labeled probe is gradually heated, and a change in signal caused by the temperature increase is measured. For example, in the case of using Q PROBE®, the fluorescence intensity in the state of being hybridized with the single-stranded DNA is decreased (or quenched) as compared to the fluorescence intensity in the dissociated state. Therefore, for example, the hybrid emitting decreased fluorescence or the quenched hybrid may be gradually heated, and an increase in fluorescence intensity caused by the temperature increase may be measured. In a case of using the labeled probe, the signal value may be measured under conditions based on a labeled substance for the labeled probe.

The temperature range in which the change in fluorescence intensity is measured is not particularly limited, and the initial temperature may be, for example, a temperature of from room temperature to 85° C., or a temperature of from 25° C. to 70° C. The final temperature may be, for example, a temperature of from 40° C. to 105° C. The temperature increase rate is not particularly limited, either, and may be, for example, in the range of from 0.1° C./sec to 20° C./sec, or in the range of from 0.3° C./sec to 5° C./sec.

In the Tm value measurement process, the change in the signal obtained from the measurement process is analyzed to determine the Tm value. More specifically, the Tm value may be determined by calculating a differential value at each temperature (−d (Fluorescence Intensity)/dt) from the fluorescence intensity obtained, and taking the temperature at which the differential value takes the lowest value as the Tm value. Alternatively, for example, an amount of change in fluorescence intensity per unit time at each temperature may be calculated. In a case where as the amount of change, "−d (amount of increase in fluorescence intensity)/dt" is adopted, a temperature associated with the resulting lowest derivative value may be determined as the Tm value. In a case where as the amount of change, "d (amount of increase in fluorescence intensity)/dt" is adopted, a temperature associated with the resulting highest derivative value may be determined as the Tm value. On the other hand, when a labeled probe that is used is not a quenching probe, but is a probe which does not show a signal by itself and shows a signal when hybridized, a decrease in fluorescent intensity can be measured.

Tm value may be calculated by a conventional known software manufactured by MELTCAL (http://www.meltcalc.com/) or the like, or by the nearest neighbor method.

In the polymorphism detection process, the presence of a polymorphism of EGFR exon 19 is detected based on the determined Tm value. In the optional polymorphism abundance ratio detection process, the abundance ratio of the single-stranded nucleic acid including a polymorphism of EGFR exon 19 is detected based on the determined Tm value.

Not only evaluating the dissociation temperature of a hybrid, but also evaluating the degree of the derivative value of a fluorescence signal that changes based on temperature during melting of a hybrid is included. The abundance ratio of a base sequence (DNA) having a polymorphism may be evaluated depending on the derivative value.

In the present invention, a change in signal caused by a temperature increase (preferably an increase in fluorescence intensity) may be measured while heating the hybrid as described above. Alternatively, instead of this method, the measurement of a change in signal may alternatively be carried out, for example, in the course of hybrid formation. In other words, the temperature of the sample, to which the probe has been added, may be decreased, and a change in signal caused by the temperature decrease may be measured in the course of hybrid formation.

In a specific example, when a labeled probe which shows a signal by itself but does not shows a signal when hybridized (for example Q Probe®) is used, the probe emits fluorescence when a single-stranded nucleic acid sequence and a labeled probe are dissociated, and when the probe is hybridized by lowering the temperature, the fluorescence is decreased (or quenched). Therefore, for example, a decrease in fluorescence intensity caused by temperature decrease may be measured while gradually decreasing the temperature of the heated sample. On the other hand, when a labeled probe which does not show a signal by itself and shows a signal when hybridized is used, the probe does not emit fluorescence when a single strand nucleic acid sequence and a labeled probe are dissociated, and when the probe is hybridized by lowering the temperature, the probe emits fluorescence. Thus, for example, by gradually lowering the temperature of the reaction solution, increase of fluorescent intensity can be measured.

In quantitative measurement of abundance ratio of nucleic acid sequence of a mutant-type and wild-type EGFR exon 19, each of a mutant-type and wild-type nucleic acid sequence is preliminarily provided to produce each calibration curve, and then each abundance ratio is preferably detected.

An example of producing a calibration curve will be described below.

First, for example, plural nucleic acid mixtures are prepared that each have different abundance ratios of two types of nucleic acid, a wild-type nucleic acid Wt and a mutant nucleic acid Mt. Melting curves are obtained with a melting curve analysis instrument for each of the plural nucleic acid mixtures.

Figure 1B:
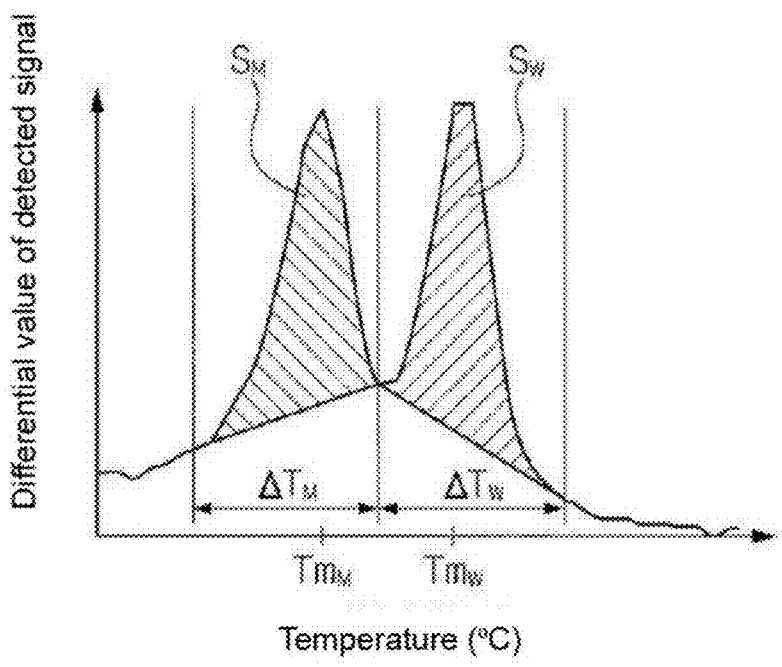
FIG. 1B shows an example of a differential melting curve.
Figure 2A:
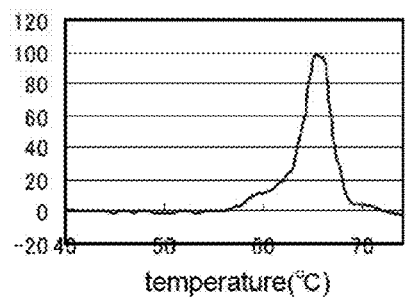
FIG. 2A shows the differential melting curve of the sample of Example 1 according to the present invention.
Figure 2B:
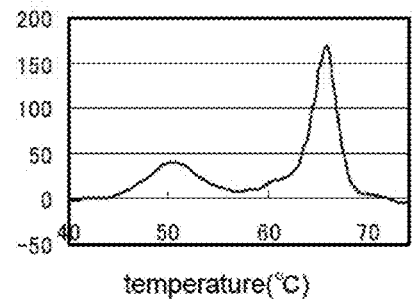
FIG. 2B shows the differential melting curve of the sample of Example 1 according to the present invention.
Figure 2C:
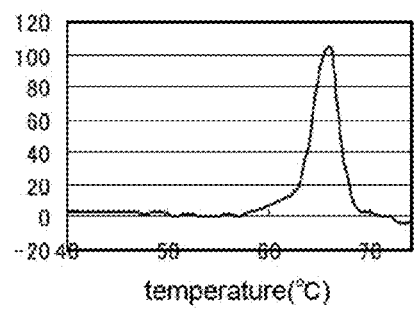
FIG. 2C shows the differential melting curve of the sample of Example 1 according to the present invention.
Figure 2D:
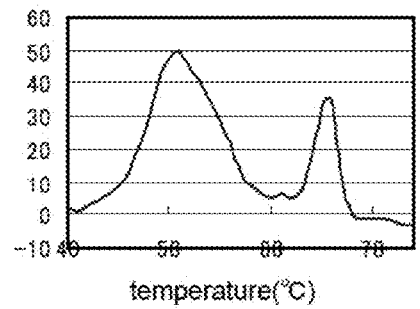
FIG. 2D shows the differential melting curve of the sample of Example 1 according to the present invention.
Figure 3A:
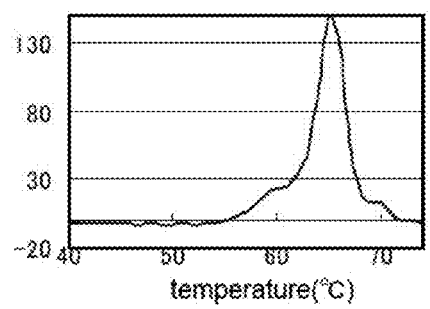
FIG. 3A shows the differential melting curve of the sample of Example 2 according to the present invention.
Figure 3B:
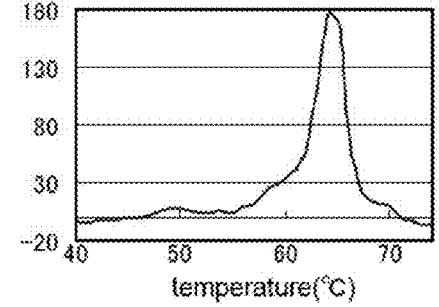
FIG. 3B shows the differential melting curve of the sample of Example 2 according to the present invention.
Figure 3C:
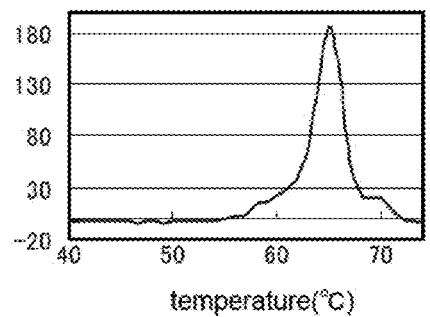
FIG. 3C shows the differential melting curve of the sample of Example 2 according to the present invention.
Figure 3D:
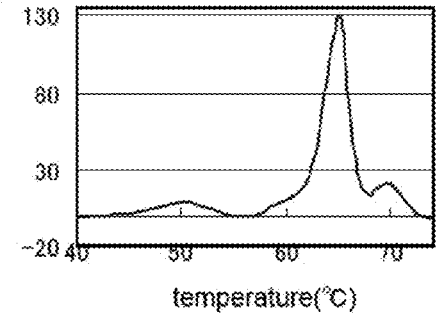
FIG. 3D shows the differential melting curve of the sample of Example 2 according to the present invention.
Figure 7A:
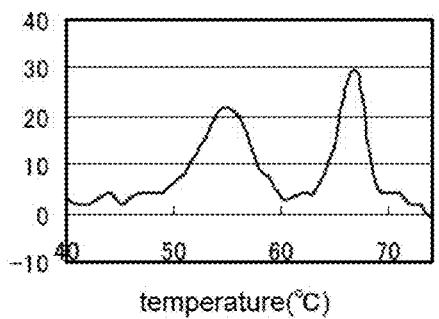
FIG. 7A shows the differential melting curve of the sample of Comparative Example 3 according to the present invention.
Figure 7B:
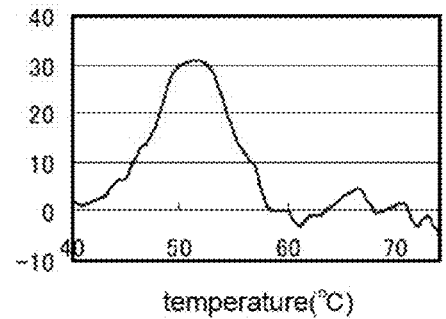
FIG. 7B shows the differential melting curve of the sample of Comparative Example 3 according to the present invention.
Figure 7C:
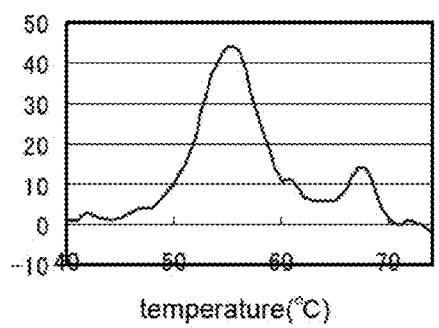
FIG. 7C shows the differential melting curve of the sample of Comparative Example 3 according to the present invention.
Figure 7D:
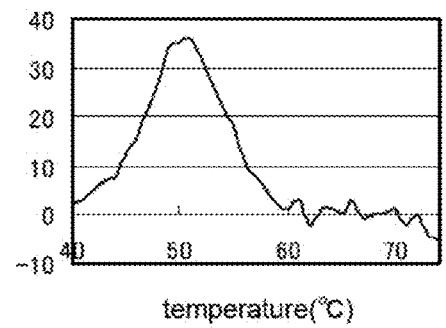
FIG. 7D shows the differential melting curve of the sample of Comparative Example 3 according to the present invention.

FIG. 1A illustrates a melting curve expressing the relationship for a single nucleic acid mixture of a detection signal, such as a degree of light absorption or fluorescence intensity, to temperature. FIG. 1B illustrates a melting curve (also called a differential melting curve) expressing the relationship of the differential values of the detection signal to temperature. The melting temperature $Tm_W$ of the nucleic acid Wt and the melting temperature $Tm_M$ of the mutant nucleic acid Mt are detected from the peaks of the differential melting curve. Temperature ranges are then set to contain $Tm_W$ and $Tm_M$, respectively.

As a temperature range $\Delta T_W$ containing $Tm_M$ a temperature range can be set, for example, with a lower limit at the temperature at which the differential value of the detection signal reaches a minimum between $Tm_W$ and $Tm_M$, and an upper limit at the temperature corresponding to the tail of the detection signal peak. As the temperature range $\Delta T_M$ containing $Tm_M$, a temperature range can be set, for example, with an upper limit at the temperature at which the differential value of the detection signal reaches a minimum between $Tm_W$ and $Tm_M$, and with a lower limit at a temperature corresponding to the tail of the detection signal peak.

The temperature range $\Delta T_W$ and the temperature range $\Delta T_M$ can be set so as to have the same width as each other (for example 10° C.) or set to have different widths from each other (for example a temperature range $Tm_W$ of 10° C., and a temperature range $Tm_M$ of 7° C.). The temperature range $\Delta T_W$ and the temperature range $\Delta T_M$ can be set with widths from minus X° C. to plus X° C. from the temperature range Tm or the temperature range Tw, respectively, (for example, 15° C. or less, or preferably 10° C. or less).

Then, for each of the temperature range $\Delta T_W$ and the temperature range $\Delta T_M$, respectively, a surface area is derived of an area bounded by a straight line passing through a point corresponding to the lower limit and a point corresponding to the upper limit of the respective temperature range of the differential melting curve and bounded by the differential melting curve itself (the shaded regions in FIG. 1B). A specific example of a method that can be employed for deriving the surface area is set out below. Derivation can be made according to the following Equality (1), in which f (T) is a differential value of the detection signal at temperature T, and B (T) is a base value at temperature T.

Surface Area $S=\{f(T_{s+1})-B(T_{s+1})\}+\{f(T_{s+2})-B(T_{s+2})\}$
and so on up to $\{f(T_{e-1})-B(T_{e-1})\}$  Equality (1)

In Equality (1), $T_s$ is the lower limit value of each of the temperature ranges, and $T_e$ is the upper limit value thereof. The base value B (T) at each temperature T is a value derived according to the following Equality (2), and represents the background level included in the detection signal. Influence from background included in the detection signal is removed by subtracting this base value from the differential value of the detection signal.

$B(T)=a\times(T-T_s)+f(T_s)$  Equality (2)

In Equality (2), $a=\{f(T_e)-f(T_s)\}/(T_e-T_s)$.

For each nucleic acid mixture the surface area $S_W$ over the temperature range $\Delta T_W$ and the surface area $S_M$ over the temperature range $\Delta T_M$ are derived according to Equality (1) and Equality (2). A detection amount curve is then generated expressing the relationship between the area ratios and the abundance ratios for each of the nucleic acid mixtures. For example, the detection amount curve may be one with the abundance ratio (the proportion of nucleic acid Mt to the total nucleic acid mixture) on the horizontal axis and the area ratio $(S_M/S_W)$ on the vertical axis. A detection amount curve such as this is stored in the memory 26. The area ratio may also be defined as $(S_W/S_M)$.

The area ratio may be calculated from the melting curve and the differential melting curve obtained from real samples to determine the abundance ratio of base sequence having polymorphism in real samples based on the above preliminarily produced calibration curve.

The abundance ratio may also be calculated in accordance with presence of each peak in the wild-type and mutant-type nucleic acids. Alternatively, the presence (existence or non-existence) of polymorphism of EGFR gene may be detected by only confirming the presence of a peak.

<Method of Evaluating EGFR Tyrosine Kinase Inhibitor>

The method of evaluating an EGFR tyrosine kinase inhibitor according to the present invention includes detecting a polymorphism of an EGFR gene by the method of detecting a polymorphism (polymorphism detection process); and evaluating tolerance to an EGFR tyrosine kinase inhibitor or efficacy of an EGFR tyrosine kinase inhibitor based on the result of the detection (drug efficacy evaluation process).

The above polymorphism detection method allows convenient and high-sensitive detection of a polymorphism of EGFR exon 19 using the oligonucleotide for a detection test of a polymorphism according to the present invention, and thereby it is possible to conveniently and high-sensitively evaluate an EGFR tyrosine kinase inhibitor based on the EGFR exon 19 polymorphism.

Description of the polymorphism detection process in the method of evaluating an EGFR tyrosine kinase inhibitor is the same as in the method of detecting a polymorphism of an EGFR gene.

It is known that EGFR tyrosine kinase activity is different depending on a polymorphism of EGFR exon 19. Particularly, in the case of a mutant-type EGFR gene, it is evaluated that a EGFR tyrosine kinase inhibitor is expected to have a cytoreductive effect.

The method of evaluating an EGFR tyrosine kinase inhibitor according to the present invention allows more highly reliable and convenient prediction about an effect of an EGFR tyrosine kinase inhibitor.

An EGFR tyrosine kinase inhibitor agents to be evaluated for drug efficacy may specifically inhibit an EGFR tyrosine kinase, and include gefitinib, erlotinib, or the like.

A typical method of evaluating polymorphism of exon 19 EGFR has been known, and is described in for example, Journal of Thoracic Oncology: March 2006—Volume 1—Issue 3—pp 260-267 (EGFR Mutation of Tumor and Serum in Gefitinib-Treated Patients with Chemotherapy-Naive Non-small Cell Lung Cancer).

<Reagent Kit>

The reagent kit for a detection test of a polymorphism of EGFR for detecting a polymorphism of an EGFR gene of the present invention encompasses the above oligonucleotide for a detection test of a polymorphism.

The reagent kit includes the above oligonucleotide for a detection test of a polymorphism that is hybridizable to the amplification inhibition target region, which can be used to conveniently and highly sensitively detect a polymorphism of EGFR exon 19, and thereby more convenient detection of a polymorphism of an EGFR gene is achieved.

The reagent kit may also include a probe that is hybridizable to a region including a polymorphism site in the target EGFR gene, and further include a primer set capable of amplifying a nucleic acid containing the polymorphism site in the target EGFR gene. The reagent for a detection test of a polymorphism according to the present invention can thus conveniently and highly sensitively detect a polymorphism in the EGFR gene. Regarding the probe and primers that can be included in the reagent kit, those described above may be employed without change.

Each reagent in the reagent kit may be contained in a different container, or in the same container. The term "different container" may refer to one that is divided so as to maintain each reagent in a non-contact condition, and such a container may not necessarily be an individual container that can be handled independently.

In addition to the above, the reagent kit may include reagents such as polymerases or buffers necessary for amplification, reagents or buffers necessary for hybridization, and diluents for diluting a specimen sample. The reagent kit also preferably includes a manual describing the above polymorphism detection method or instructions about each reagent included or that can be additionally included in the kit.

EXAMPLES

The present invention will now be described in detail by way of Examples, but the present invention is not restricted thereto. The "part" or "%" is by mass unless otherwise specified.

Examples 1 to 3

PCR and Tm analysis were carried out by using a thermal cycler (trade name: MASTERCYCLER EP GRADIENT S produced by EPPENDORF), a fully automated SNP detection system (trade name: i-densy (trademark) produced by ARKRAY) and reagents for detection prepared by prescriptions described in Tables 3 to 5 below. The used polymerase is Taq polymerase.

PCR was carried out by conducting the treatment at 95° C. for 60 seconds, and then repeating a cycle of 95° C. for 1 second and 54° C. for 15 seconds 50 times.

Tm analysis was carried out by conducting the treatments at 95° C. for 1 second and at 40° C. for 60 seconds after the PCR, subsequently raising the temperature from 40° C. to 75° C. at a temperature rising rate of 1° C. per 3 seconds, and the change with time of the fluorescent intensity during the elevation of the temperature was measured. The change of the fluorescent intensity originated from the fluorescently labeled probe was measured respectively by using an excitation wavelength of 420 nm to 485 nm and a measurement wavelength of 520 to 555 nm. It is known that a peak at about 66° C. is observed for the wild type gene and peaks at about 51° C. and about 66° C. are observed for the mutant type gene.

As an oligonucleotide for a detection test of a polymorphism according to the present invention used to inhibit the nucleic acid amplification of a single-stranded nucleic acid in the sample (hereinafter referred to as "WI nucleic acid"), Cmp-1 (SEQ ID NO: 2, Example 1) having the same sequence as that of the region from the 104th to the 143rd base in SEQ ID. NO: 1, Cmp-2 (SEQ ID NO: 3, Example 2) having the same sequence as that of the region from the 104th to the 132nd base in SEQ ID. NO: 1, or Cmp-3 (SEQ ID NO: 4, Example 3) having the same sequence as that of the region from the 115th to the 142nd base in SEQ ID. NO: 1 was used in an amount of 0.2 µM or 0.4 µM respectively.

The sequence of the wild type EGFR exon 19 is as shown in SEQ ID NO: 1.

E746_A750del was used as the mutant type EGFR exon 19 (Table 2, No. 2).

5FP-EGFR-EX19-WT-FW-3 (5'-(FL)-CCCGTCGCTAT-CAAGTAATTAAGAGAAGCAACA: SEQ ID NO: 35) which recognizes the sequence of the region from the 104th to the 136th base in SEQ ID. NO: 1 and has a label at 5'-end was used as a probe. EGFR-EX19-F2 (TCTCTCTGTCATAGG-GACTC: SEQ ID NO: 33) corresponding to the sequence of the region from the 54th to the 73rd base in SEQ ID. NO: 1 was used as F primer (forward primer), and EGFR-EX19-R1 (GAAACTCACATCGAGGATTTC: SEQ ID NO: 34) corresponding to the sequence of the region from the 155th to the 175th base in SEQ ID. NO: 1 was used as R primer (reverse primer). As a template nucleic acid sequence, $1 \times 10^3$ copy/µL of purified human genome (produced by ROCHE), and $1 \times 10^3$ copy/µL of plasmid (manufactured by GENESCRIPT) obtained by mixing the wild type gene sequence (SEQ ID NO: 1) and the mutant type gene sequence (SEQ ID NO: 36 corresponding to No. 2 in Table 2) at a ratio of 10:990 (the mixing ratio of the mutant type: 1%) were used.

Each sequence is as described in Table 6.

Graphs showing the amounts of the change in fluorescence of the probe were obtained by the Tm analysis.

The results are shown in FIG. 2 to FIG. 4. FIG. 2A, FIG. 3A and FIG. 4A, and FIGS. 2C, 3C and FIG. 4C show the cases that only genomic DNA was used as the template nucleic acid sequence (wild type 100%), and FIG. 2B, FIG. 3B and FIG. 4B, and FIGS. 2D, 3D and FIG. 4D show the cases that the plasmid DNA obtained by mixing the wild type gene sequence and the mutant type gene sequence at a prescribed ratio was used as the template nucleic acid sequence. In each Figure, FIG. 2A, FIG. 3A and FIG. 4A, and FIG. 2B, FIG. 3B and FIG. 4B show the cases that the concentration of the WI nucleic acid is 0.2 µM, and FIGS. 2C, 3C and FIG. 4C, and FIGS. 2D, 3D and FIG. 4D show the cases that the concentration of the WI nucleic acid is 0.4 µM. In the Figures, the abscissa indicates the temperature (° C.), and the ordinate indicates the amount of the change in fluorescence.

TABLE 3

| Example 1 | | |
|---|---|---|
| (Amount of reaction solution 10 µl) | Sample 1-0.2 | Sample 1-0.4 |
| 1 × PCR buffer | | |
| dNTP | 0.2 mM | 0.2 mM |
| MgCl2 | 1.5 mM | 1.5 mM |
| Taq polymerase | 0.0376U | 0.0376U |
| probe | 0.1 µM | 0.1 µM |
| F primer | 1 µM | 1 µM |

TABLE 3-continued

Example 1

| (Amount of reaction solution 10 μl) | Sample 1-0.2 | Sample 1-0.4 |
|---|---|---|
| R primer | 4 μM | 4 μM |
| Cmp-1 | 0.2 μM | 0.4 μM |

TABLE 4

Example 2

| (Amount of reaction solution 10 μl) | Sample 2-0.2 | Sample 2-0.4 |
|---|---|---|
| 1 × PCR buffer | | |
| dNTP | 0.2 mM | 0.2 mM |
| MgCl2 | 1.5 mM | 1.5 mM |
| Taq polymerase | 0.0376U | 0.0376U |
| probe | 0.1 μM | 0.1 μM |
| F primer | 1 μM | 1 μM |
| R primer | 4 μM | 4 μM |
| Cmp-2 | 0.2 μM | 0.4 μM |

TABLE 5

Example 3

| (Amount of reaction solution 10 μl) | Sample 3-0.2 | Sample 3-0.4 |
|---|---|---|
| 1 × PCR buffer | | |
| dNTP | 0.2 mM | 0.2 mM |
| MgCl2 | 1.5 mM | 1.5 mM |
| Taq polymerase | 0.016U | 0.016U |
| probe | 0.1 μM | 0.1 μM |
| F primer | 1 μM | 1 μM |
| R primer | 4 μM | 4 μM |
| Cmp-3 | 0.2 μM | 0.4 μM |

TABLE 6

| | (5'→3') | mer | SEQ ID No. |
|---|---|---|---|
| WI nucleic acid | | | |
| Cmp-1 | CCCGTCGCTATCAAGGAATTAAGAGAAGCAACATCTCCGA-(P) | 40 | 2 |
| Cmp-2 | CCCGTCGCTATCAAGTAATTAAGAGAAGC-(P) | 29 | 3 |
| Cmp-3 | CAAGGAATTAAGAGAAGCAACATCTCCG-(P) | 28 | 4 |
| Cmp-C1 | TAAGAGAAGCAACATCTCCGAAAGCCAAC-(P) | 29 | 32 |
| Primer | | | |
| F primer | TCTCTCTGTCATAGGGACTC | 20 | 33 |
| R primer | GAAACTCACATCGAGGATTTC | 21 | 34 |
| Probe | | | |
| Probe | CCCGTCGCTATCAAGTAATTAAGAGAAGCAACA | 33 | 35 |

As shown in FIG. 2 and FIG. 3, a peak was observed only at about 66° C. for the nucleic acid sample containing the genomic DNA alone (wild type 100%), and a peak at about 51° C. was further clearly observed for the nucleic acid sample containing the plasmid DNA (mutant type 1%). It was revealed that the same tendency was observed even though the concentration of the WI nucleic acid was changed, and the mutant type nucleic acid sequence could be detected with higher sensitivity by increasing the concentration of the WI nucleic acid.

As shown in FIG. 4, in Example 3 in which the concentration of the DNA polymerase was changed to 0.16 U which is no more than half the concentrations in Examples 1 and 2, the peak of the mutant type nucleic acid was revealed to be observed more clearly compared to the peaks in Example 1 and Example 2.

From the above-described Examples, the numbers of the overlapping bases between the probe used and the WI nucleic acid sequence were 33 mer (Cmp-1, 100%), 29 mer (Cmp-2, 87.9%) and 22 mer (Cmp-2, 66.7%), respectively. This result revealed that when the ratio of the numbers of the overlapping bases between the probe and the WI nucleic acid sequence is not less than 66.7% (22 mer/33 mer), the mutant type nucleic acid could be detected with high sensitivity.

Comparative Example 1 to Comparative Example 4

In Comparative Example 1, the detection of polymorphism was carried out in the same manner as in Example 1 except that Cmp-C1 having the same sequence as that of the region from the 123rd to the 151st base in SEQ ID. NO: 1 (SEQ ID NO: 32, see Table 6) was used as the WI nucleic acid sequence. The result is shown in FIG. 5.

In Comparative Example 2, the detection of polymorphism was carried out in the same manner as in Example 1 except that a reaction solution containing no WI nucleic acid sequence and no probe was used, and the probe was added in a final amount of 104 to each sample after the PCR reaction. Each component in the reagent for the PCR reaction is shown in Table 7. The result is shown in FIG. 6.

In Comparative Example 3, the detection of polymorphism was carried out in the same manner as in Example 1 except that Cmp-C1 having the same sequence as that of the region from the 123rd to 151st base in SEQ ID. NO: 1 was used as the WI nucleic acid sequence, and the concentration of the DNA polymerase was changed to 0.16 U. The result is shown in FIG. 7.

Figure 8A:
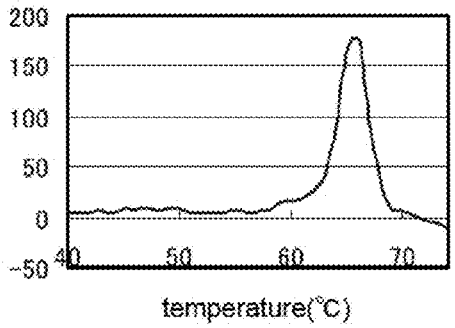
FIG. 8A shows the differential melting curve of the sample of Comparative Example 4 according to the present invention.
Figure 8B:
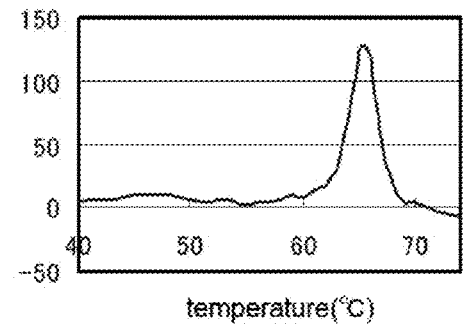
FIG. 8B shows the differential melting curve of the sample of Comparative Example 4 according to the present invention.

In Comparative Example 4, the detection of polymorphism was carried out in the same manner as in Comparative Example 2 except that 0.16 U of the DNA polymerase was used. The result is shown in FIG. 8.

In FIG. 5 to FIG. 8, FIG. 5A, FIG. 6A, FIG. 7A and FIG. 8A, and FIG. 5C, FIG. 6C, FIG. 7C and FIG. 8C show the cases that only genomic DNA was used as the template nucleic acid sequence (wild type 100%), and FIG. 5B, FIG. 6B, FIG. 7B and FIG. 8B, and FIG. 5D, FIG. 6D, FIG. 7D and FIG. 8D show the cases that a plasmid DNA obtained by mixing the wild type gene sequence and the mutant type gene sequence at a prescribed ratio was used as the template nucleic acid sequence. In each Figure, FIG. 5A, FIG. 6A, FIG. 7A and FIG. 8A, and FIG. 5B, FIG. 6B, FIG. 7B and FIG. 8B show the cases that the concentration of the WI nucleic acid is 0.2 μM, and FIG. 5C, FIG. 6C, FIG. 7C and FIG. 8C, and FIG. 5D, FIG. 6D, FIG. 7D and FIG. 8D show the cases that the concentration of the WI nucleic acid is 0.4 μM. In the Figs., the abscissa indicates the temperature (° C.), and the ordinate indicates the amount of the change in fluorescence.

TABLE 7

Comparative Example 2

| (Amount of reaction solution 10 μl) | Sample C1 |
|---|---|
| 1 × PCR buffer | |
| dNTP | 0.2 mM |
| MgCl2 | 1.5 mM |
| Taq polymerase | 0.0376U |
| F primer | 1 μM |
| R primer | 4 μM |

As shown in FIG. 5, when the WI nucleic acid sequence which did not contain the sequence corresponding to the sequence of the amplification inhibition target region at from the 115th to the 123rd in SEQ ID. NO: 1 was used, a peak at 61° C. indicating the mutant type was observed in both cases where the genomic DNA was used and where the plasmid DNA was used as the template nucleic acid sequences, and the judgment could not be made.

The numbers of the overlapping bases between the WI nucleic acid sequence Cmp-C1 for comparison used in Comparative Example 1 and the polymorphism detection probe was 14 mer, and the ratio of the numbers of the overlapping bases between the polymorphism detection probe and the WI nucleic acid sequence was 42.4% (14 mer/33 mer). From this result, it was revealed that when the ratio of the numbers of the overlapping bases between the WI nucleic acid sequence and the polymorphism detection probe is 42.4% (14 mer/33 mer), a peak indicating the wild type was not observed.

As shown in FIG. 6, when PCR reaction had been carried out in the absence of the WI nucleic acid, a peak indicating the mutant type was not observed and the mutant type could not be detected.

The same tendency was obtained even though the amount of the DNA polymerase was decreased (see FIG. 7 and FIG. 8).

Example 4

The PCR reaction and Tm analysis were carried out by using the fully automated SNP detection system (trade name: i-densy (trademark), produced by ARKRAY), and the detection of a polymorphism was carried out in the same manner as in Example 1 except that samples A to J in which the types of the template nucleic acid sequence were changed as shown in Table 8 (see Table 8 for the sequence of the mutant type plasmid, and see SEQ ID NO: 1 for the sequence of the wild type plasmid) were used, and each component in the PCR reaction solution was changed as shown in Table 9. The used polymerase was Taq polymerase.

As the template nucleic acid sequence in each sample, 1×10³ copy/μL of plasmid obtained by mixing the wild type gene sequence (SEQ ID NO: 1) and each mutant type gene sequence shown in Table 8 at a mixing ratio shown in Table 8 (produced by GENESCRIPT) was used. As for the types of the mutant type gene described in Table 8, No. 2 and No. 3 indicate E746_A750del, No. 4 indicates L747_E749del, A750P, and No. 6 indicates L747_S752del, P753S (see Table 2).

It is known that a peak at about 66° C. is observed for the wild type gene, and peaks at about 51° C. and at about 66° C. are observed respectively for the mutant type gene depending on the types of the mutant type gene.

The results are shown in FIG. 9 and FIG. 10.

TABLE 8

| | | Types of mutated type gene | Mixing ratio (%) | Note |
|---|---|---|---|---|
| Sample A | Human genome | — | 0.0 | — |
| Sample B | Plasmide | No. 2 | 0.3 | SEQ ID No. 36 |
| Sample C | Plasmide | No. 3 | 0.3 | SEQ ID No. 37 |
| Sample D | Plasmide | No. 4 | 0.3 | SEQ ID No. 38 |
| Sample E | Plasmide | No. 6 | 0.3 | SEQ ID No. 39 |
| Sample F | Plasmide | No. 2 | 0.1 | SEQ ID No. 36 |
| Sample G | Plasmide | No. 2 | 1.0 | SEQ ID No. 36 |
| Sample H | Plasmide | No. 2 | 5.0 | SEQ ID No. 36 |
| Sample I | Plasmide | No. 2 | 10.0 | SEQ ID No. 36 |
| Sample J | Plasmide | No. 2 | 50.0 | SEQ ID No. 36 |

TABLE 9

Example 4

| (Amount of reaction solution 10 μl) | |
|---|---|
| 1 × PCR buffer | |
| dNTP | 0.14 mM |
| MgCl2 | 1.07 mM |
| Taq polymerase | 0.016U |
| probe | 0.07 μM |
| F primer | 0.71 μM |
| R primer | 2.86 μM |
| Cmp-1 | 0.14 μM |

As shown in FIG. 9, only a peak at about 66° C. was observed for Sample A containing only the wild type gene (see FIG. 9A), and on the other hand, a clear peak at 51 to 54° C. indicating each mutant type gene was observed in addition to a peak at about 66° C. for samples B to E (FIG. 9B to FIG. 9E) containing each mutant type gene. It was revealed that the mutant type could be detected by using the WI nucleic acid sequence regardless of the types of the mutant type gene.

As shown in FIG. 10, it was revealed that even though the mixing ratios of the mutant type gene were changed to 0.1%, 1%, 5%, 10% and 50%, the mutant type genes could be detected mixing ratio-dependently as peaks each having a height depending on the mixing ratio (see FIG. 10A to FIG. 10E).

Example 5 and Comparative Example 5

The PCR reaction and Tm analysis were carried out by using the fully automated SNP detection system (trade name: i-densy (trademark), produced by ARKRAY), and the detection of a polymorphism was carried out in the same manner as in Example 1 except that a PCR reaction solution in which the concentration of the WI nucleic acid was changed to 0.03 μM, 0.06 μM, 0.12 μM or 0.18 μM (Samples 5-1 to 5-4, Example 5), or a PCR reaction solution which does not contain the WI nucleic acid (samples 5-5, Comparative Example 5) was used, and the probe was added in an final amount of 1 μM per sample after PCR reaction. As the nucleic acid sample, a plasmid DNA containing the mutant type (No. 2) and the wild type at a mixing ratio of 1% of the mutant type was used. The prescription of each sample is shown in Table 10.

The results are shown in FIG. 11. FIG. 11A shows the result of sample 5-1 in which the concentration of the WI nucleic acid is 0.03 μM, FIG. 11B shows the result of sample 5-2 in which the concentration of the WI nucleic acid is 0.06 μM, FIG. 11C shows the result of sample 5-3 in which the concentration of the WI nucleic acid is 0.12 μM, FIG. 11D shows the result of sample 5-4 in which the concentration of the WI nucleic acid is 0.18 μM, and FIG. 11E shows the result of sample 5-5 in which the concentration of the WI nucleic acid is 0.

TABLE 10

| Example 5 | | | | |
|---|---|---|---|---|
| (Amount of reaction solution 10 μl) | Sample 5-1 | Sample 5-2 | Sample 5-3 | Sample 5-4 |
| 1 × PCR buffer | | | | |
| dNTP | 0.2 mM | 0.2 mM | 0.2 mM | 0.2 mM |
| MgCl2 | 1.5 mM | 1.5 mM | 1.5 mM | 1.5 mM |
| Taq polymerase | 0.021U | 0.021U | 0.021U | 0.021U |
| F primer | 1 μM | 1 μM | 1 μM | 1 μM |
| R primer | 4 μM | 4 μM | 4 μM | 4 μM |
| Cmp-1 | 0.03 μM | 0.06 μM | 0.12 μM | 0.18 μM |

As shown in FIGS. 11A to D, both of the peak at about 66° C. indicating the wild type and the peak at about 51° C. indicating the mutant type are observed for Samples 5-1 to Sample 5-4 containing the WI nucleic acids having different concentrations. It can be seen that the peaks of the mutant type become higher depending on the concentrations of the WI nucleic acid.

Figure 11A:
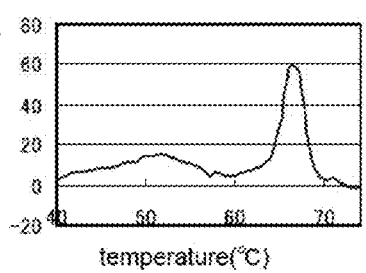
FIG. 11A shows the differential melting curve of a sample 5-1 of Example 5 according to the present invention.
Figure 11B:
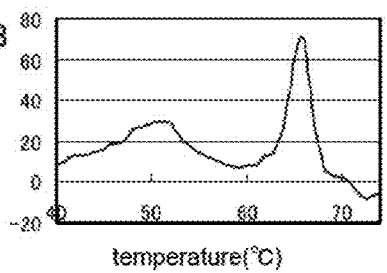
FIG. 11B shows the differential melting curve of a sample 5-2 of Example 5 according to the present invention.
Figure 11C:
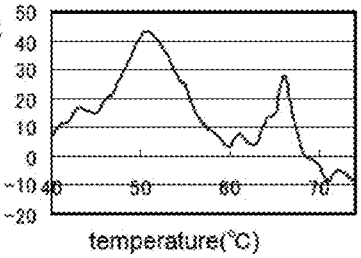
FIG. 11C shows the differential melting curve of a sample 5-3 of Example 5 according to the present invention.
Figure 11D:
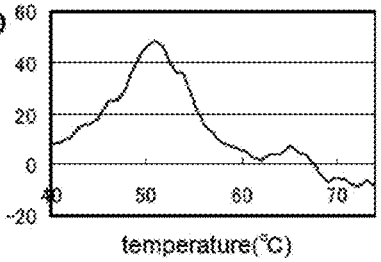
FIG. 11D shows the differential melting curve of a sample 5-4 of Example 5 according to the present invention.
Figure 11E:
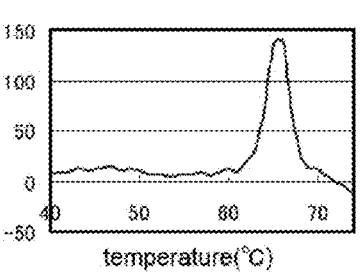
FIG. 11E shows the differential melting curve of a sample 5-5 of Comparative Example 5 according to the present invention.

On the other hand, as shown in FIG. 11E, a peak at about 51° C. indicating the mutant type was not clear for Sample 5-5 which does not contain the WI nucleic acid.

Thus, according to the present invention, the polymorphism in EGFR exon 19 can be detected easily with high sensitivity.

All references, patent applications, and technical standards described in the present specification are herein incorporated in their entirety by reference into the specification, to the same extent as if each individual reference, patent application or technical standard was specifically and individually indicated to be incorporated herein by reference.

What is claimed is:

1. A reagent kit comprising:
An oligonucleotide consisting of a nucleotide sequence selected from the group consisting of SEQ ID NO: 2 to 16 and having a 3' end subjected to an extension inhibition treatment, and;
a probe comprising SEQ ID NO: 35 that is labeled with a fluorescent dye.

2. The reagent kit according to claim 1, further comprising a primer set that amplifies a nucleic acid sequence having a target polymorphic site in EGFR exon 19.

3. The reagent kit of claim 1, wherein the oligonucleotide consists of a nucleotide sequence selected from the group consisting of SEQ ID NO: 2 to 4.

4. The reagent kit of claim 1, wherein the probe consists of SEQ ID NO: 35 that is labeled with a fluorescent dye.

5. The reagent kit according to claim 1, wherein the extension inhibition treatment is addition of a phosphate group.

6. The reagent kit according to claim 1, wherein the oligonucleotide includes a base labeled with a fluorescent dye.

7. The reagent kit according to claim 1, wherein the oligonucleotide consists of a nucleotide sequence of SEQ ID NO: 2.

8. The reagent kit according to claim 1, wherein the oligonucleotide consists of a nucleotide sequence of SEQ ID NO: 3.

9. The reagent kit according to claim 1, wherein the oligonucleotide consists of a nucleotide sequence of SEQ ID NO: 4.

10. A method of detecting a polymorphism in EGFR exon 19, the method comprising contacting a sample comprising an EGFR exon 19 nucleic acid with the oligonucleotide and probe from the reagent kit of claim 1.

11. The method of detecting a polymorphism in EGFR exon 19 according to claim 10, wherein the method comprises:
providing a sample nucleic acid which contains a single-stranded nucleic acid having the base sequence shown in SEQ ID NO: 1; and
performing a nucleic acid amplification of the sample nucleic acid in the presence of the probe and the oligonucleotide.

12. The method of detecting a polymorphism in EGFR exon 19 according to claim 10, wherein the probe emits fluorescence when not hybridized with a target sequence thereof, and a fluorescence intensity decreases when the probe hybridizes with the target sequence thereof.

13. A method of evaluating the drug efficacy of or tolerance to an EGFR tyrosine kinase inhibitor, the method comprising:
detecting a polymorphism in EGFR exon 19 by the method of claim 10, and;
evaluating tolerance to the EGFR tyrosine kinase inhibitor or efficacy of the EGFR tyrosine kinase inhibitor based on a result of the detection.

* * * * *